(12) United States Patent
Isobe

(10) Patent No.: US 11,334,629 B2
(45) Date of Patent: May 17, 2022

(54) SEARCH SYSTEM FOR CHEMICAL COMPOUND HAVING BIOLOGICAL ACTIVITY

(71) Applicant: HITACHI HIGH-TECH SOLUTIONS CORPORATION, Tokyo (JP)

(72) Inventor: Takashi Isobe, Pleasanton, CA (US)

(73) Assignee: HITACHI HIGH-TECH SOLUTIONS CORPORATION, Tokyo (JP)

(*) Notice: Subject to any disclaimer, the term of this patent is extended or adjusted under 35 U.S.C. 154(b) by 284 days.

(21) Appl. No.: 16/728,097

(22) Filed: Dec. 27, 2019

(65) Prior Publication Data

US 2021/0200809 A1 Jul. 1, 2021

(51) Int. Cl.
| | |
|---|---|
| *G06F 16/9035* | (2019.01) |
| *G06F 16/9038* | (2019.01) |
| *G06N 5/02* | (2006.01) |
| *G06K 9/62* | (2022.01) |
| *G06F 16/901* | (2019.01) |
| *G16H 50/70* | (2018.01) |

(52) U.S. Cl.
CPC ........ *G06F 16/9035* (2019.01); *G06F 16/901* (2019.01); *G06F 16/9038* (2019.01); *G06K 9/6215* (2013.01); *G06K 9/6232* (2013.01); *G06N 5/02* (2013.01); *G16H 50/70* (2018.01)

(58) Field of Classification Search
CPC ............. G06F 16/9035; G06F 16/9038; G06F 16/901; G06N 5/02; G06K 9/6215; G06K 9/6232; G16H 50/70
USPC ......................................................... 707/722
See application file for complete search history.

(56) References Cited

U.S. PATENT DOCUMENTS

| | | | |
|---|---|---|---|
| 2006/0074859 A1 | 4/2006 | Gange et al. | |
| 2006/0224562 A1* | 10/2006 | Yan | G16C 20/40 |
| 2019/0303780 A1* | 10/2019 | Spangler | G06N 20/00 |
| 2020/0272702 A1* | 8/2020 | Takeda | G16C 20/80 |

OTHER PUBLICATIONS

Sander, Thomas, et al., "DataWarrior: An Open-Source Program for Chemistry Aware Data Visualization and Analysis", Journal of Chemical Information and Modeling, Jan. 5, 2015, ©American Chemical Society, pp. 460-473.*
Hattori, Masahiro, et al., "SIMCOMP/SUBCOMP: chemical structure search servers for network analyses", Nucleic Acids Research, vol. 38, Web Server Issue, May 11, 2020, pp. W652-W656.*
Sam, Elizabeth, et al., "Web-based drug repurposing tools: a survey", Briefings in Bioinformatics, © 2017, published by Oxford University Press, pp. 1-18.*

(Continued)

*Primary Examiner* — Robert Stevens
(74) *Attorney, Agent, or Firm* — Mattingly & Malur, PC

(57) ABSTRACT

In a search system for a chemical compound having a biological activity, a chemical compound searcher calculates feature vectors distances between a feature vector of a specified chemical compound recorded on an exemplar table and feature vectors of the chemical compounds recorded on a search table and obtains similar chemical compounds in response to the feature vectors distances. A GUI displays the similar chemical compounds and information representing biological activities of the similar chemical compounds.

21 Claims, 17 Drawing Sheets

(56) References Cited

OTHER PUBLICATIONS

Hessler, Gerhard, et al., "The scaffold hopping potential of pharmacophores", Drug Discovery Today: Technologies, vol. 7, No. 4, © 2010 Elsevier, Ltd, pp. e263-e269.*
Microsoft Computer Dictionary, 5th Edition, © 2002, Microsoft Corporation, Redmond, WA, pp. 239 and 510.*
Willett, Peter, et al., "Chemical Similarity Searching", J. Chem. Inf. Comput. Sci., vol. 38, No. 6, Jul. 1998, pp. 983-996.*
Yan, Xifeng, et al., "Structure Similarity in Graph Databases", SIGMOD 2005, Baltimore, MD, Jun. 14-16, 2005, pp. 766-777.*
Sander, Thomas, et al., "OSIRIS, an Entirely in-House Developed Drug Discovery Informatics System", J. Chem. Inf. Model., vol. 49, No. 2, Jan. 2009, pp. 232-246.*
Thomas Scior, et al. "Recognizing Pitfalls in Virtual Screening: A Critical Review", Journal of Chemical Information and Modeling, Mar. 21, 2012, 52 (4), pp. 867-881.
David K. Johnson, et al., "Ultra-High-Throughput Structure-Based Virtual Screening for Small-Molecule Inhibitors of Protein-Protein Interactions", Journal of Chemical Information and Modeling, Jan. 4, 2016, 56 (2), pp. 399-411.
Peter Willett, "Similarity-Based Virtual Screening Using 2D Fingerprints", Drug Discovery Today, Dec. 2006, vol. 11, Issues 23-24, 19 pages.
Hans Matter, et al., "Comparing 3D Pharmacophore Triplets and 2D Fingerprints for Selecting Diverse Compound Subsets", Journal of Chemical Information and Computer Sciences, 1999, vol. 39, No. 6, pp. 1211-1225.
Japanese Office Action received in corresponding Japanese Application No. 2020-183449 dated Nov. 30, 2021.

\* cited by examiner

Fig. 3

Exemplar Table — 300, 301-1

Chemical Compound #1

- 302: ID
- 303: Name
- 304: InChI

Ring Structures (305)
- 309: Hydrocarbon 6-Mbr Rings
- 310: Hydrocarbon 5-Mbr Rings
- 311: Hydrocarbon 3-Mbr Rings
- 312: 6-Mbr Rings with $N_1$
- 313: 5-Mbr Rings with $N_1$
- 314: 6-Mbr Rings with $N_2$
- 315: 5-Mbr Rings with $N_2$
- 316: 6-Mbr Rings with NO
- 317: 5-Mbr Rings with NO
- 318: 6-Mbr Rings with S
- 319: 5-Mbr Rings with S
- 355: Rings

Chain Structures (306)
- 320: Methyl Grps
- 321: Hydrocarbon (-CH2-) Chains
- 322: Oxo Grps
- 323: Carbonyl Grps
- 324: Aldehyde Grps
- 325: Carboxy Grps
- 326: Hydroxy Grps
- 327: Acetyl Grps
- 328: Amino Grps
- 329: Nitro Grps
- 330: Cyano Grps
- 331: Halogeno Grps
- 332: Ester Bonds
- 333: Amide Bonds
- 334: Urethane Bonds
- 335: POx Bonds
- 336: SOx Bonds
- 337: Ethyl/Methyl Ether Bonds

Pharmacophores (354)
- 338: 6-Mbr Ring Ether Bonds
- 339: 5-Mbr Ring Ether Bonds

Physical/Chemical Features (307)
- 340: Solubility
- 341: Boiling Point
- 342: Freezing Point
- 343: Molar Mass

Biological Activity (308)
- 344: Existence
- 345: Biological Response A
- 346: Biological Response B
- 347: Biological Effect Level A
- 348: Biological Effect Level B

⋮

Chemical Compound #N — 301-N

Fig. 16

Input GUI — 1600

| | |
|---|---|
| Threshold for Single Biological Activity | 1.0 |
| Threshold for Plural Biological Activities | 1.0 |

Search Table to be used    ● Table X    ○ Table Y    ○ Table Z

Mask / Weight:  1, 1, 1, 1, 1, 1, 1, 1, 2, 1, 1, 0, 1, 1

Differential Feature Amount:  0, 0, 5, 0, -4, 0, 0, 0, 0, 0, 0, 0, 0, 0, 0

Exemplar Chemical Compound A of Exemplar Table

- ☐ Chemical Compound A-1
- ☑ Chemical Compound A-2
- ☑ Chemical Compound A-3
- ☐ Chemical Compound A-4

Exemplar Chemical Compound B of Exemplar Table

- ☑ Chemical Compound B-1
- ☐ Chemical Compound B-2
- ☐ Chemical Compound B-3
- ☑ Chemical Compound B-4

SEARCH SYSTEM FOR CHEMICAL COMPOUND HAVING BIOLOGICAL ACTIVITY

BACKGROUND

Technical Field

The present invention relates to a search system for chemical compound having biological activity.

Background Art

A search system for a chemical compound having a biological activity is called virtual screening and classified into a technique based on similarity to existing chemical compounds like ligands and a technique for three-dimensional simulation of docking with a target protein using information of structure or polarity, according to "Recognizing Pitfalls in Virtual Screening: A Critical Review" by T. Scior, A. Bender, G. Tresadern, et al., from "Journal of Chemical Information and Modeling" 2012 52 (4), 867-881 and "Ultra-High-Throughput Structure-Based Virtual Screening for Small-Molecule Inhibitors of Protein-Protein Interactions" by David K. Johnson and John Karanicolas, from "Journal of Chemical Information and Modeling" 2016 56 (2), 399-411. The technique for determining similarity to existing chemical compounds can improve accuracy by increasing the amount of data about chemical compounds having biological activities. The technique for three-dimensional simulation of docking with target protein is suitable in searching unknown chemical compounds having a new structure.

A technique called "Fingerprint" is well known as a technique to calculate the similarity to existing chemical compounds. "Similarity-based virtual screening using 2D fingerprints" by Peter Willett, from "Drug Discovery Today", Volume 11, Issues 23-24, December 2006, Pages 1046-1053 describes a screening method using 2D fingerprint to measure structural similarity. "Comparing 3D Pharmacophore Triplets and 2D Fingerprints for Selecting Diverse Compound Subsets" by Hans Matter and Thorsten Poetter, from "Journal of Chemical Information and Computer Sciences" 1999 39 (6), 1211-1225 describes 3D pharmacophoric triplets (PDTs) fingerprint.

SUMMARY OF THE INVENTION

Problems to be Solved by the Invention

Conventional similarity measurement uses fingerprint wherein existence of various structural features such as rings, chains and pharmacophores is represented by 1 or 0. This technique has a problem that compounds significantly different in numbers of structural features or physical/chemical features (molar mass, boiling point, freezing point, vapor pressure, density, water solubility, organic solvent solubility, thermal stability, acidity/alkalinity, spectrum, etc.) are determined to be chemical compounds with high similarity, resulting in a lower accuracy.

Also, although conventional similarity measurement can measure similarity with respect to a single chemical compound, there is a problem in a case wherein there are a plurality of chemical compounds having a specific biological activity that what chemical compound with how much of what feature should be a typical chemical compound.

Moreover, although conventional similarity measurement can achieve high accuracy in a chemical compound space where it can acquire a large amount of biological activity data, most of biological activity data is often kept closed by each organization and there are few compound spaces having a sufficient amount of biological activity data. Therefore, conventional techniques have a problem that they cannot determine prospect of chemical compound candidates having some biological activity and unknown new structures objectively in a chemical compound space where there is little biological activity data.

Means for Solving the Problems

A search system for a chemical compound having a biological activity related to an embodiment of the present invention comprises:

a search table and an exemplar table, wherein the search table and the exemplar table record information representing structural features or physical/chemical features for a plurality of chemical compounds, and wherein the search table and the exemplar table can further record information representing a biological activity including a biological response or a biological effect level;

a chemical compound searcher, wherein the chemical compound searcher:
  obtains at least one chemical compound as a specified chemical compound based on the chemical compounds recorded on the exemplar table;
  obtains feature vectors representing the structural features or the physical/chemical features for the specified chemical compound and the chemical compound recorded on the search table;
  calculates a feature vector distance between the feature vector of the specified chemical compound and each chemical compound recorded on the search table; and
  obtains a chemical compound recorded on the search table as a similar chemical compound in response to the feature vectors distances, and a GUI for displaying the similar chemical compound and information representing a biological activity of the similar chemical compound.

Another embodiment of the present invention realizes search for chemical compounds similar to a known chemical compound having a biological activity in a high accuracy by using a feature vectors distance (e.g. a Euclidian distance) for feature vectors having a number of various structural features (ring structures, chain structures and pharmacophores) and physical/chemical features (molar mass, boiling point, freezing point, vapor pressure, density, water solubility, organic solvent solubility, thermal stability, acidity/alkalinity, spectrum, etc.) as feature amounts.

Yet another embodiment of the present invention realizes search for a typical chemical compound having a specific biological activity by: calculating the feature vectors distances between a plurality of exemplar chemical compounds having the specific biological activity and a plurality of chemical compounds included in a chemical compound space; searching chemical compounds included in the chemical compound space which minimize a sum or an average of the feature vectors distances as similar chemical compounds; and presenting the similar chemical compounds together with their feature vectors.

Yet another embodiment of the present invention realizes search in a chemical compound space around a chemical compound candidate having an unknown new structure by allowing customization of the feature vector of an exemplar chemical compound by adding a differential feature amount.

Yet another embodiment of the present invention calculates feature vectors distances between a plurality of exemplar chemical compounds having respectively different biological activity and a plurality of chemical compounds included in a chemical compound space and performs a search in a chemical compound space including a common similar chemical compound with small feature vectors distances to the plurality of the exemplar chemical compounds at the same time.

Yet another embodiment of the present invention calculates a biological activity information existence rate for a plurality of similar chemical compounds and calculates a deviation from the biological activity information existence rate of the entire chemical compound space to provide an indication for determining prospect of the chemical compound spaces including the similar chemical compounds.

Effects of the Invention

According to an embodiment of the invention, a feature vectors distance (a Euclidian distance, etc.) is used for feature vectors including, as feature amounts, not only numbers of various structural features (rings, chains and pharmacophores, etc.) but also physical/chemical features (molar mass, boiling point, freezing point, vapor pressure, density, water solubility, organic solvent solubility, thermal stability, acidity/alkalinity, spectrum, etc.), thereby allowing search for chemical compounds having high similarity in both the number of structural features and the physical/chemical features with a high accuracy.

According to another embodiment of the invention, feature vectors distances are calculated between a plurality of exemplar chemical compounds having a specific biological activity and a plurality chemical compounds included in a chemical compound space; a chemical compound which minimizes a sum or an average of the feature vectors distances among the chemical compounds in the chemical compound space as a similar chemical compound; and the similar chemical compound is presented together with its feature vector, thereby realizing search for a typical chemical compound having the specific biological activity.

According to yet another embodiment of the invention, a feature vector of an exemplar chemical compound can be customized by adding a differential feature amount, thereby allowing search in a chemical compound space around a chemical compound candidate having a new unknown structure.

According to yet another embodiment of the invention, feature vectors distances are calculated between a plurality of exemplar chemical compounds having respectively different biological activities and a plurality of chemical compounds included in a chemical compound space and search is performed in a chemical compound space including a common similar chemical compound which has short feature vectors distances to the plurality of exemplar chemical compounds at the same time, thereby allowing search for a chemical compound candidate having a new unknown structure even if the feature vectors distances to the exemplar chemical compounds are relatively long.

According to yet another embodiment of the invention, biological activity information existence rates are calculated for a plurality of similar chemical compounds and deviations from the biological activity information existence rates of entire chemical compound spaces is calculated, thereby providing an indication for measuring prospect of chemical compound spaces including the similar chemical compounds. Accordingly, the prospect regarding whether a chemical compound having a new structure has some biological activity can be measured even in an unknown chemical compound space wherein there is no biological activity data available.

Problems, constructions and effects other than the above will become apparent from the following description of embodiments and the accompanying figures.

BRIEF DESCRIPTION OF THE DRAWINGS

FIG. 3 is a format of an exemplar table of the first embodiment;

FIG. 16 is a GUI for inputting, by a user, a threshold for feature vectors distances (distance threshold), information for selecting a search table to be used, an original chemical compound, weight values for masking or weighting feature amounts, and differential feature amounts for creating unknown feature amounts in the first embodiment.

DETAILED DESCRIPTION

Figure 1:
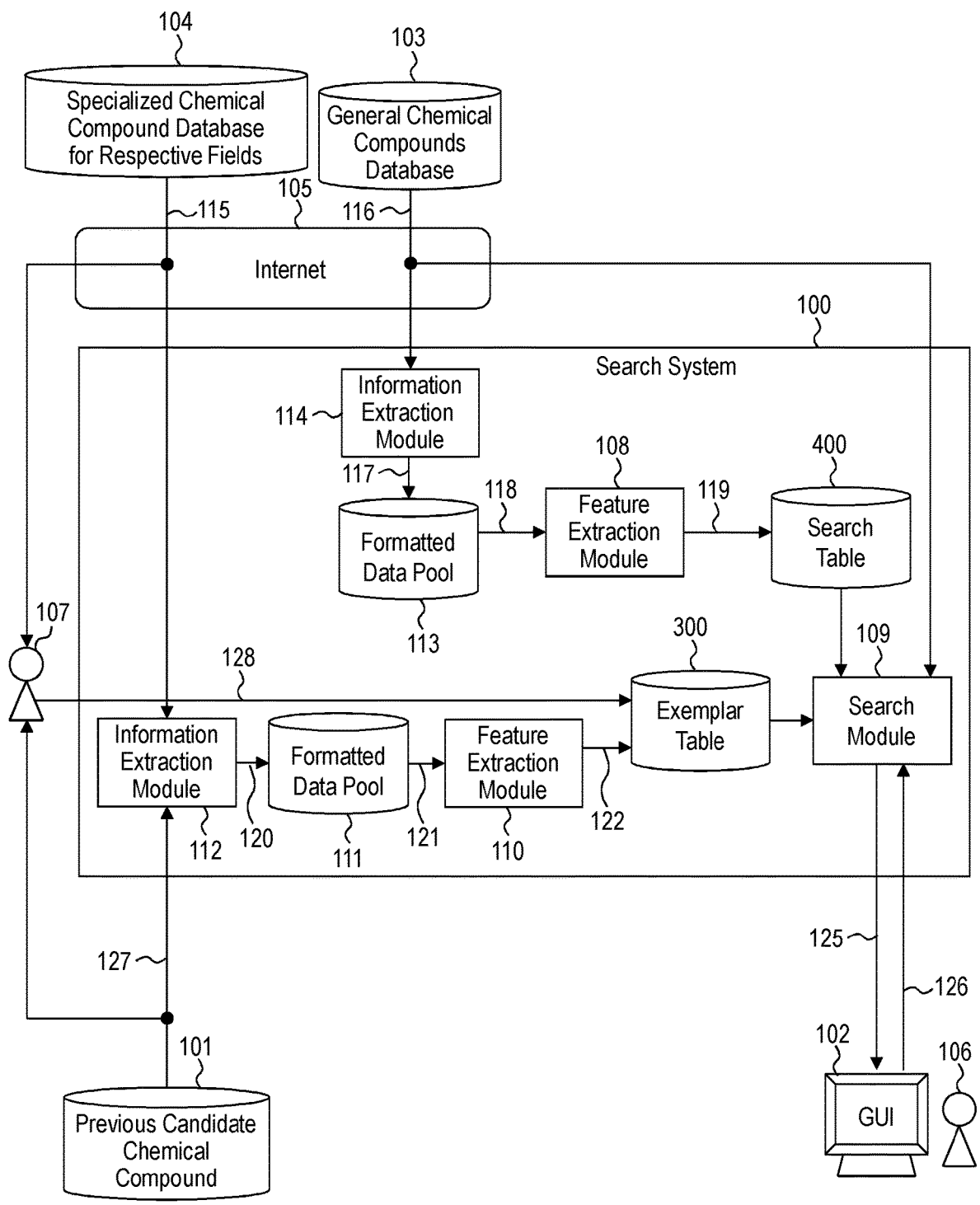
FIG. 1 is a schematic diagram of a search system of a first embodiment.

Below, embodiments of the present invention will be explained in detail with reference to the accompanying figures. In the respective figures, identical constructions may be given identical reference characters.

First Embodiment

In a first embodiment, an embodiment of a basic system related to the present invention will be explained.

FIG. 1 is a schematic diagram of a search system 100 for chemical compounds (or chemical compound candidates) having biological activities.

As shown in FIG. 1, the search system 100 for chemical compounds having biological activities comprises information extraction modules 114,112, formatted data pools 113, 111, feature extraction modules 108,110, an exemplar table 300, a search table 400 and a search module 109. Further, the search system 100 is connected to a previous candidate chemical compound table 101 owned by a user and a GUT 102. Also, the search system 100 is connected to specialized chemical compound database 104 for respective fields and a general chemical compounds database 103 through the Internet 105 (or another communication network).

The search system 100 may be constructed by using a known computer. The computer may comprise an operation means and a storage means. The operation means may comprise a processor and the storage means may comprise a non-transitory storage medium and may comprise for example one or more of a semiconductor memory, a magnetic disk device, a portable storage medium, etc. If the search system 100 for chemical compounds is a computer, the storage means may store a computer program and the computer may function as the search system 100 for the chemical compounds when the operation means executes the computer program.

The specialized chemical compound database 104 for respective fields and the general chemical compound database 103 may be disclosed databases. In these databases, for example, IDs (or information identifying chemical compounds), names, structural formulas (e.g. InChI: International Chemical Identifier), physical/chemical features, biological activities, etc. are recorded for a plurality of chemical compounds. The physical/chemical feature includes, for example, molar mass, boiling point, freezing point, vapor pressure, density, water solubility, organic solvent solubility, thermal stability, acidity/alkalinity and spectrum. The biological activity may be information referred to as "bioassay" and includes a biological response and a biological effect level. The specialized chemical compound database 104 for respective fields and the general chemical compound database 103 may be in any form, and for example include data in an SDF format.

The information extraction module 114 reads data 116 from the general chemical compound database 103, extracts data 117 including information representing an ID, a name, a structural formula, physical/chemical features and biological activities for each chemical compound and records the data 117 on the formatted data pool 113. The data 117 includes information for each chemical compound representing whether or not there is information regarding any biological activity.

The information representing whether or not there is information regarding any biological activity may be created based on information other than the general chemical compound database 103. For example, if a published patent application or a published article includes a name of chemical compound or a specific string related to a chemical compound (e.g. an abbreviation, a structural formula or a symbol of element), it may be recorded that there is information regarding the biological activity for the chemical compound. In this manner, a biological activity not registered in the general chemical compound database 103 can also be utilized.

The feature extraction module 108 reads data 118 from the formatted data pool 113 and records information of chemical compounds onto the search table 400 based on the data 118. The search table 400 records data 119 including information representing structural features or physical/chemical features for a plurality of chemical compounds. Further, the data 119 may include, fix at least a part of the chemical compounds, information regarding biological activity. That is, the search table 400 can record information representing the biological activity.

The structural feature is represented by information regarding molecular structure of the chemical compound and includes, for example, one or more numbers regarding ring structures (ring systems), one or more numbers regarding chain structures, or one or more numbers regarding pharmacophores. The structural feature may be obtained by analyzing a structural formula such as InChI.

The numbers regarding ring structures may include a number of six-membered rings, a number of five-membered rings, a number of four-membered rings, a number of three-membered rings, etc. Also, the numbers may be classified based on whether the ring includes a specific element or on the number of the specific element included, and for example the numbers may include a number of six-membered rings including exactly one nitrogen atom, a number of six-membered rings including exactly two nitrogen atoms, a number of five-membered rings including exactly one nitrogen atom and a number of five-membered rings including exactly two nitrogen atoms. Also, the numbers may include, for example, a number of six-membered rings including nitrogen and oxygen, a number of five-membered rings including nitrogen and oxygen, a number of six-membered rings including sulfur, a number of five-membered rings including sulfur, etc.

The number regarding chain structures may include a number of substituent groups, a number of functional groups, a number of characteristic groups, etc. For example, a number of methyl groups, a number of oxo groups, a number of ester bonds, a number of amide bonds, etc. may be included.

The pharmacophore may mean an aggregate combining ring structures and chain structures and the numbers regarding the pharmacophores may include a number of ether bonds with six-membered rings, a number of ether bonds with five-membered rings, etc.

The physical/chemical features include a physical feature or a chemical feature. The physical/chemical feature may include molar mass, boiling point, freezing point, vapor pressure (or saturated vapor pressure), density, water solubility, organic solvent solubility, thermal stability, acidity/alkalinity or spectrum. The spectrum for example represents a wavelength wherein an intensity is strongest within a spectrum of a reflecting wave if an X-ray of a predetermined wavelength is irradiated on the chemical compound.

Thus, using various factors as information representing the structural features or the physical/chemical features enables a search in a higher accuracy.

The biological activity includes a biological response and a biological effect level. The biological response may be information representing a type of response of a specific creature, protein, enzyme or biosynthetic circuit with respect to the chemical compound. The biological effect level may be information representing an amount of the chemical compound necessary to cause a specific biological response.

The previous candidate chemical compound table 101 may be a private database owned by the user and may be closed. The previous candidate chemical compound table 101 records, for example, data in the format same as the specialized chemical compound database 104 for respective fields or the general chemical compounds database 103.

The information extraction module 112 reads data 115 from the specialized chemical compound database 104 for respective fields, or reads data 127 from the previous candidate chemical compound table 101, extracts information for each chemical compound representing an ID, a name, a structural formula, a physical/chemical feature and a biological activity and records the extracted data 120 onto the formatted data pool 111. The data 120 also includes information regarding whether or not there is information regarding any biological activity for each chemical compound. A format of the formatted data pool 111 may be similar to the formatted data pool 113.

The feature extraction module 110 reads data 121 of the formatted data pool 111 and records information of the chemical compounds onto the exemplar table 300 based on the data 121. A format of the exemplar table 300 may be similar to the search table 400. That is, data 122 including information representing the structural features or the physical/chemical features is recorded on the exemplar table 300 for a plurality of chemical compounds. Further, the data 122 may include, for at least a part of the chemical compounds, information regarding biological activity. That is, the exemplar table 300 can record information representing the biological activity.

The exemplar table 300 may record, as an alternative to or in addition to the information recorded by the feature extraction module 110, information recorded by a human operator 107. For example, the operator 107 reads the data 115 from the specialized chemical compound database 104 for respective fields or the data 127 from the previous candidate chemical compound table 101 and may record manually-formatted data 128 onto the exemplar table 300. Creating data 128 based on chemical compounds of various fields allows utilizing the search system 100 for various applications without changing the construction of the search 100 significantly.

Via the GUI 102, the user 106 may transmit a search command 126 for searching chemical compounds to the search module 109 of the search system 100. The GUI 102 may be constructed by using a well-known computer, display device, etc. The GUI 102 receives the inputted search command 126 and transmits this to the search module 109. The search command 126 includes information specifying a chemical compound of the exemplar table 300, information specifying a biological activity regarding a chemical compound of the exemplar table 300, information specifying a threshold for feature vectors distances, information specifying a substituent group, functional group or characteristic group to be added or replaced, etc.

The search module 109 is an example of a chemical compound searcher. The search module 109 obtains a feature vector representing various structural features (a number of rings, a number of chains or a number of pharmacophores) or physical/chemical features (molar mass, boiling point, freezing point, vapor pressure, density, water solubility, organic solvent solubility, thermal stability, acidity/alkalinity, spectrum, etc.) and performs a search for chemical compounds using this feature vector.

The search for the chemical compounds is performed based on feature vectors distances. For example, the search module 109 calculates a feature vectors distance between a feature vector of a user-specified chemical compound in the exemplar table 300, or a chemical compound having a user-specified biological activity in the exemplar table 300, and a feature vector of each chemical compound in the search table 400 and calculates a similarity for each chemical compounds in the search table 400 based on each feature vectors distance.

Thus, the search module 109 can search a chemical compound having a high similarity with respect to the chemical compound of the user's interest from the search table 400.

Alternatively, if there are a plurality of chemical compounds having the user-specified biological activity in the exemplar table 300, the search module 109 may determine which chemical compound is a typical chemical compound among the chemical compounds similar to the plurality of chemical compounds.

Alternatively, the search module 109 may search a chemical compound candidate having an unknown new structure, even if the feature vectors distance to the exemplar chemical compound is relatively long, by searching in a chemical compound space including a common similar chemical compound which has short feature vectors distances to a plurality of the chemical compounds in the exemplar table 300 at the same time.

Alternatively, the search module 109 may generate a feature vector of an unknown chemical compound by applying a user-specified differential feature mount with respect to the feature amount of a user-specified chemical compound in the exemplar table 300. The differential feature amount is, for example, a difference in the number of substituent, functional or characteristic groups. This construction allows determination of a chemical compound candidate that is likely to have some biological activity.

The search module 109 outputs a search result 125 to the GUI 102. This allows a search in a higher accuracy, for example of chemical compounds having a high similarity in terms of both the structural features and the physical/chemical features.

Figure 2:
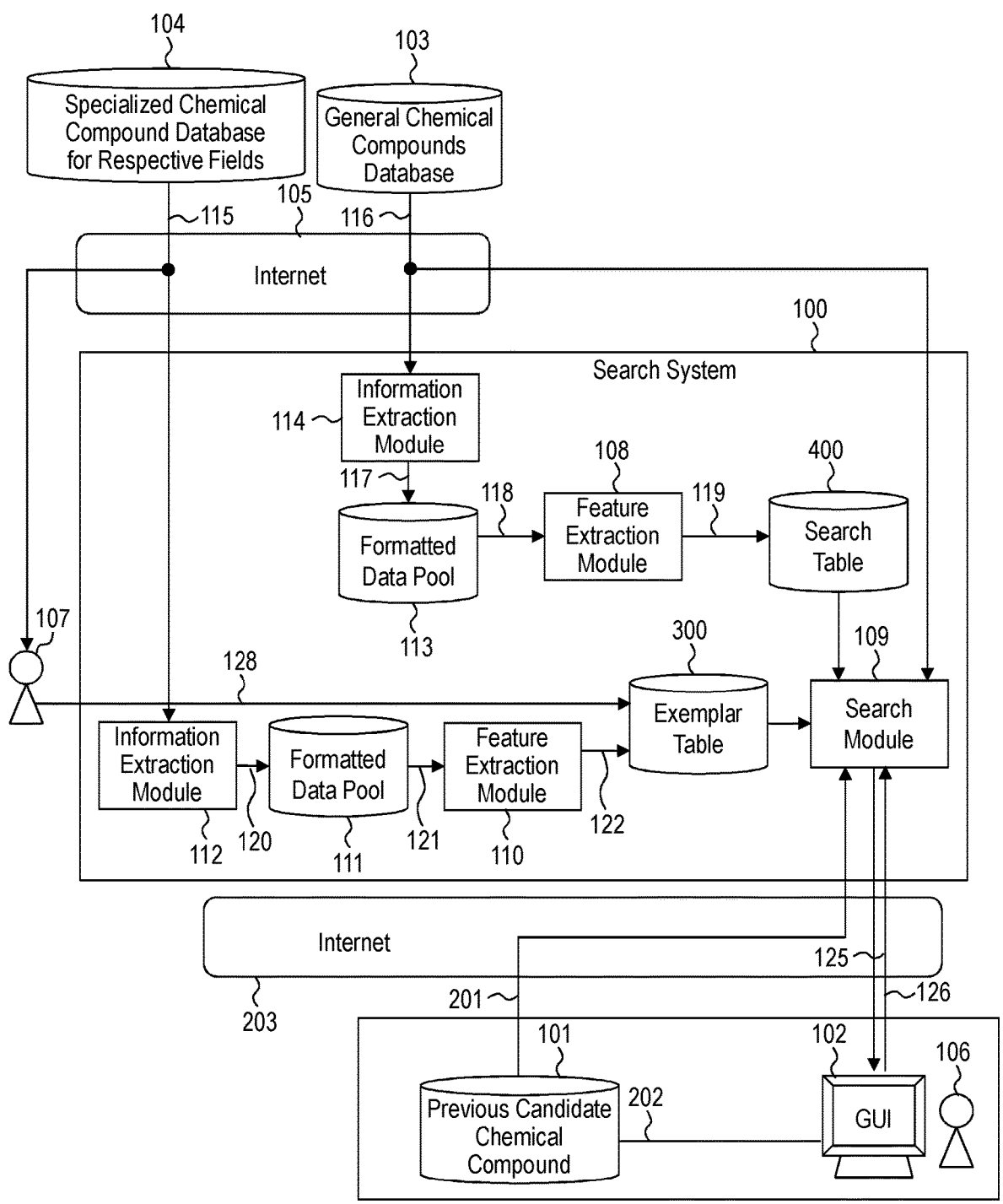
FIG. 2 is a schematic diagram of an alternative example wherein the search system of the first embodiment is provided as a cloud service.

FIG. 2 is a schematic diagram of an alternative example wherein the search system 100 for chemical compounds having biological activities is provided as a cloud service.

In the present construction, the exemplar table 300 does not include any information based on the previous candidate chemical compound table 101 which may be intellectual property of the user. Also, the previous candidate chemical compound table 101 and the GUI 102 are connected to the search system 100 via the Internet 203 (or another communication network). The previous candidate chemical compound table 101, upon receiving a command 202 from the user 106, transmits data 201 specified by the command 202 to the search module 109 of the search system 100 via the Internet 203. A part or all of the data 201 may be encrypted upon transmission. This allows providing a search service for chemical compound wherein security is further enhanced.

FIG. 3 is a format of the exemplar table 300 of the first embodiment.

The exemplar table 300 includes an entry 301 for each chemical compound. The entry 301 includes an ID number 302 identifying the chemical compound, a chemical compound name 303, an IhChI formula 304, ring structure information 305, chain structure information 306, pharmacophore information 354, physical/chemical feature information 307 and biological activity information 308. The exemplar table 300 records a plurality (for example N) of chemical compounds and the entries 301 of respective chemical compounds are shown as entries 301-1 to 301-N in FIG. 3.

The ring structure information 305 for example includes numbers of members or numbers of ring structures. The numbers of the ring structures may be classified based on the number of specific elements (nitrogen, oxygen, sulfur, etc.) included. FIG. 3 shows an example of the ring structure information 305 including a number of six-membered hydrocarbon rings 309, a number of five-membered hydrocarbon ring 310, a number of three-membered hydrocarbon rings 311, a number of six-membered rings including exactly one nitrogen atom 312, a number of five-membered rings including exactly one nitrogen ring 313, a number of six-membered rings including exactly two nitrogen atoms 314, a number of five-membered rings including exactly two nitrogen rings 315, a number of six-membered rings including one or more nitrogen atoms and one or more oxygen atoms 316, a number of five-membered rings including one or more nitrogen atoms and one or more oxygen atoms 317, a number of six-membered rings including one or more sulfur atoms 318, a number of five-membered rings including one or more sulfur atoms 319, and a number of rings 355 representing a total of the numbers of the ring structures.

The chain structure information 306 for example includes numbers of chain structures. The numbers of the chain structures may be classified based on types of the substituent groups, functional groups, characteristic groups, etc. FIG. 3 shows an example wherein the chain structure information 306 includes a number methyl groups 320, a number of hydrocarbon chains 321 (i.e. a number of $-CH_2-$), a number of structures including oxygen (a number of oxo groups 322, a number of carbonyl groups 323, a number of aldehyde groups 324, a number of carboxy groups 325, a number of hydroxy groups 326 and a number of acetyl groups 327), a number of structures including nitrogen (a number of amino groups 328, a number of nitro groups 329 and a number of cyano groups 330), a number of halogeno groups 331 representing a number of negative structures (regarding chlorine, bromine, iodine, etc.), a number of ester bonds 332, a number of amide bonds 333, a number of urethane bonds 334, a number of phosphoric acid bonds 335, a number of sulfur oxides bond 336 and a number of ethyl/methyl ether bond 337.

The pharmacophore information 354 includes a number of pharmacophores that are aggregates combining ring structures, chain structures and/or polar structures. FIG. 3 shows an example wherein the pharmacophore information 354 includes a number of ether bonds with six-membered rings 338 and a number of ether bonds with five-membered rings 339.

The physical/chemical feature information 307 is information representing a physical feature or a chemical feature and includes, for example, information of molar mass, boiling point, freezing point, vapor pressure, density, water solubility, organic solvent solubility, thermal stability, acidity/alkalinity, spectrum, etc. FIG. 3 shows an example wherein the physical/chemical feature information 307 includes solubility 340, boiling point 341, freezing point 342 and molecular weight 343.

The biological activity information 308 is information representing a biological activity and includes, for example, information of a biological response and a biological effect level. The biological activity information 308 may include an existence flag 344 representing whether the exemplar table 300 records information representing any biological activity for the chemical compound. FIG. 3 shows an example wherein the biological activity information 308 includes the existence flag 344, a type or existence 345 of a feature A representing a biological response, a type or existence 346 of a feature B representing another biological response, a biological effect level 347 regarding the feature. A and a biological effect level 348 regarding the feature B. The biological activity information 308 may have only the information of the existence flag 344, and in that case, other information may be obtained from an external database (e.g. the general chemical compounds database 103 or the specialized chemical compound database 104 for respective fields) by using the ID number 302.

The biological activity information 308 may be created based on information other than information of the exemplar table 300, the general chemical compound database 103 and the specialized chemical compound database 104 for respective fields. For example, if a published document (e.g. a patent application or an article) includes a name of chemical compound or a specific string related to a chemical compound (e.g. an abbreviation, a structural formula or a symbol of element), it may be recorded that there is information regarding the biological activity.

In that case, a document score may be calculated based on the string and the document score may be recorded for each chemical compound in the exemplar table 300. A method for calculating the document score may be designed in any manner, and for example, the document scores for the documents may be always 1 (in which case the number of the documents will be the document score of the chemical compound) or the document scores may be calculated according to a specific algorithm. This allows a biological activity not recorded on the general chemical compound database 103 to be utilized.

Figure 4:
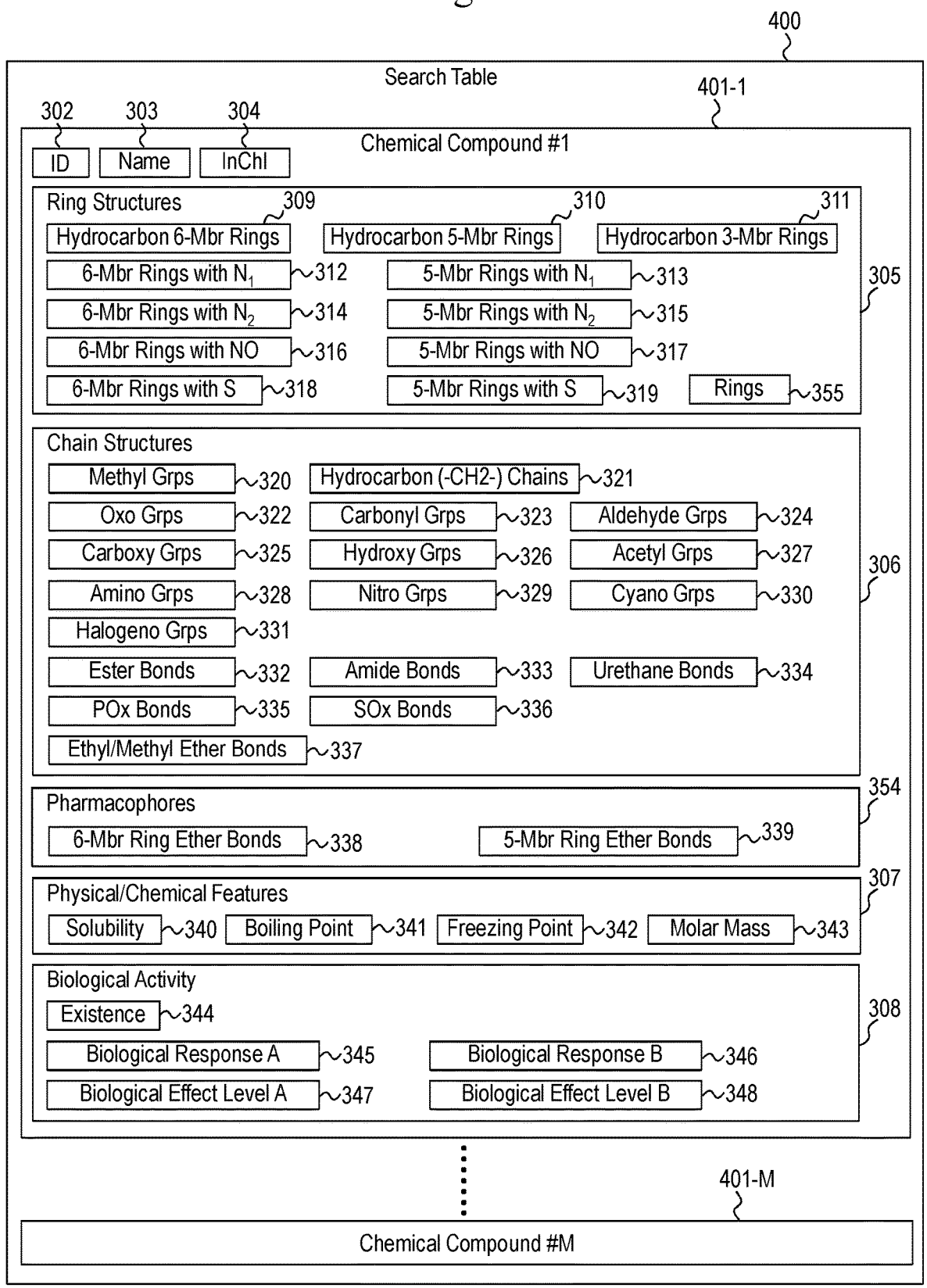
FIG. 4 is a format of a search table of the first embodiment.

FIG. 4 shows a format of the search table 400 of the first embodiment.

The search table 400 may be constructed in a format similar to the exemplar table 300. As explained in the above, the biological activity information 308 may be referred to as bioassay information representing bioassay. The search table 400 records a plurality (for example M) of chemical compounds and the entries 401 of respective chemical compounds are shown as entries 401-1 to 401-M in FIG. 4.

Figure 5:
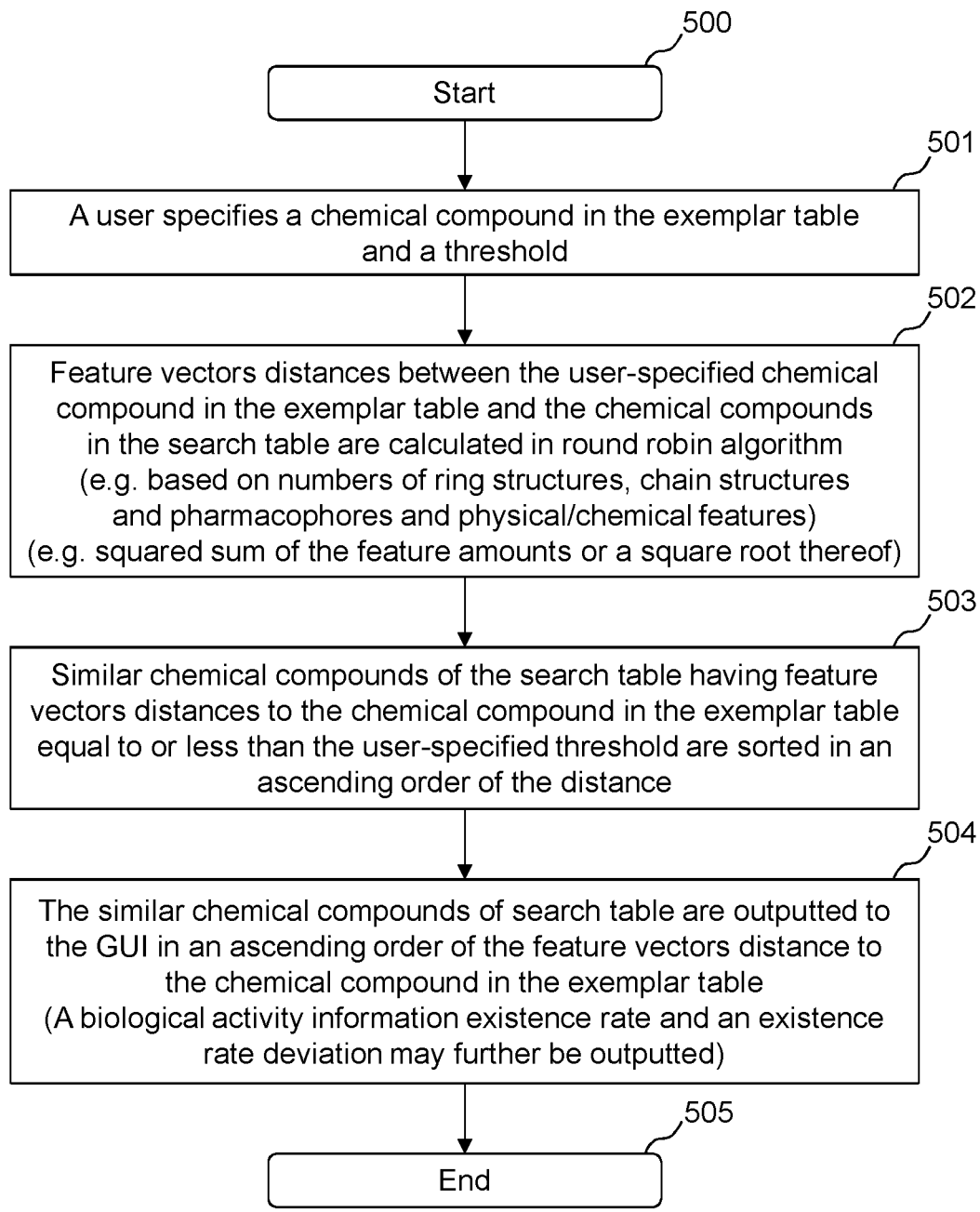
FIG. 5 is a flowchart showing a process for searching and outputting similar chemical compounds from the search table based on feature vectors distances to a user-specified biological activity in the first embodiment.

FIG. 5 is a flowchart showing a process wherein the search module 109 searches and outputs similar chemical compounds from the search table 400 based on feature vectors distances to a user-specified chemical compound in the exemplar table 300 in the first embodiment.

The search module 109, upon receiving the search command 126 from the user 106, starts the process of FIG. 5 (Step 500) and ends the process (Step 505) after outputting a search result 125 to the GUI 102.

In regard to the process of FIG. 5, the user 106 uses the search command 126 in order to specify one or more chemical compounds in the exemplar table 300 and a threshold for the feature vectors distance (distance threshold) (Step 501). The search module 109 obtains the user-specified chemical compound and the threshold via the search command 126. That is, the search module 109 obtains at least one chemical compound based on the chemical compounds recorded on the exemplar table 300. The user-specified chemical compound obtained here is referred to as a specified chemical compound hereinafter.

The search module 109 calculates the feature vectors distance between the specified chemical compound and each chemical compound in the search table 400 (Step 502). In Step 502, the search module 109 first obtains feature vectors representing structural features or physical/chemical features for the specified chemical compound and the chemical compounds recorded on the search table 400.

In the first embodiment, the feature vector includes information representing both the structural features and the physical/chemical features. The form of the feature vector may be designed in any manner, and for example, each unit of information representing the structural features and the physical/chemical features may be a feature amount and each feature amount may be an element of the feature vector. In this case, the feature vector can be constructed as a vector having a dimension which is equal to the number of information items representing the structural features and the physical chemical features. The feature vector may be normalized in any method.

In Step 502, next, the search module 109 calculates a feature vectors distance between the feature vector of the specified chemical compound and the feature vector of each chemical compound recorded on the search table 400. Let the feature vector of the specified chemical compound be X and respective feature vectors of the chemical compounds in the search table 400 be A, B, C, then the feature vectors distances X-A (representing a distance between vector X and vector A; same hereinafter), X-B, X-C are calculated.

The method for calculating the feature vectors distance for two feature vectors may be designed in any manner, and two examples are explained below. For example, this may be calculated by squaring differences between corresponding feature amounts included in the respective feature vectors (i.e. corresponding elements in the vectors) and summing them. Alternatively, this may be calculated by squaring differences between corresponding feature amounts included in the respective feature vectors, summing them and taking a square root thereof (in this case, the feature vectors distance is an Euclidian distance). In these cases, it can be said that a smaller feature vectors distance corresponds to a higher similarity.

Upon calculating the feature vectors distances, weights may be changed for a part of the feature amounts. For example, weights may be nullified by masking them (i.e. excluding them from the calculation) or weights may be increased.

The search module 109 sorts the search result (Step 503). In Step 503, the search module 109 first obtains chemical compounds recorded on the search table 400 according to the feature vectors distances. In the first embodiment, it obtains chemical compounds of the search table 400 for which the features vectors distances to the specified chemical compound are equal to or less than a user-specified threshold and sorts them in an ascending order of the feature vectors distance. The chemical compounds obtained here are hereinafter referred to as similar chemical compounds. Also, the similar chemical compounds may have some property expected by the user, so they can also be referred to as candidate chemical compounds.

The search module 109 outputs information regarding the similar chemical compounds to the GUI 102 in the sorted order (Step 504). The GUI 102 receives and displays this. For example, the GUI 102 displays the similar chemical compounds (more specifically, information representing the similar chemical compounds, and for example may be the ID numbers 302 or the chemical compound names 303) and further displays the biological activity information 308 of the similar chemical compounds. Here, the similar chemical compounds are sorted as above, so the GUI 102 can display the similar chemical compounds in an ascending order of the feature vectors distance.

Thus, the user can understand the similarities of the similar chemical compounds easily.

Note that the search module 109 may output a biological activity information existence rate and an existence rate deviation for each similar chemical compounds and GUI 102 may display them. These processes will be described later with respect to FIG. 7, etc.

Figure 6:
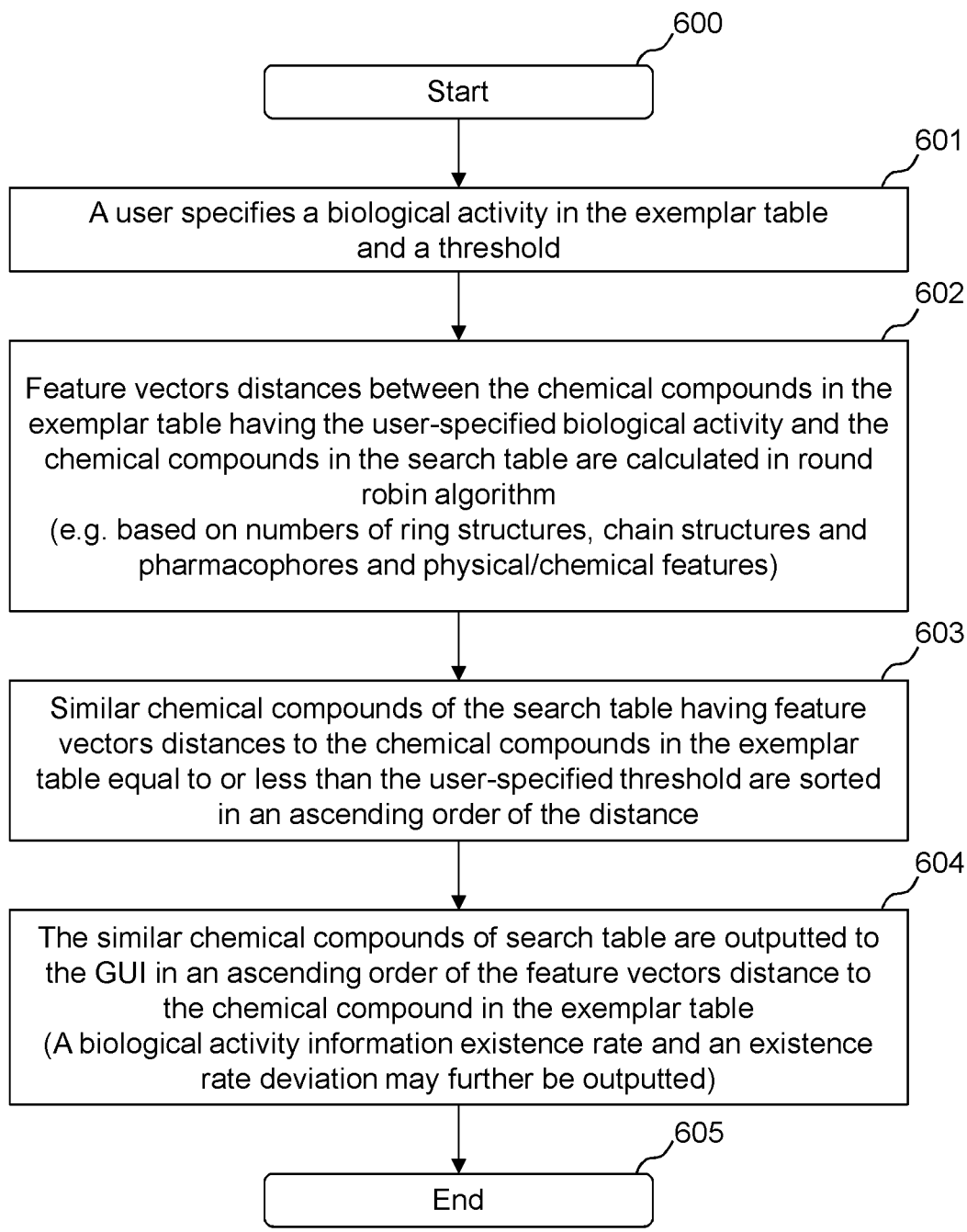
FIG. 6 is a flowchart showing a process for searching and outputting similar chemical compounds from the search table based on feature vectors distances to chemical compounds having a user-specified biological activity in the first embodiment.

FIG. 6 is a flowchart showing a process for searching and outputting the similar chemical compounds from the search table 400 based on the feature vectors distances to the specified chemical compounds.

The search module 109, upon receiving the search command 126 from the user 106, starts the process of FIG. 6 (Step 600) and ends the process (Step 605) after outputting a search result 125 to the GUI 102.

In regard to the process of FIG. 6, the user 106 uses the search command 126 in order to specify a biological activity included in any biological activity information 308 recorded for any chemical compound of the exemplar table 300 and a threshold for the feature vectors distance (Step 601). The search module 109 obtains the user-specified biological activity via the search command 126.

The biological activity is specified for example by specifying a specific biological response or by specifying a specific biological effect level regarding a specific biological response. That is, the search module 109 obtains at least one biological activity. The user-specified biological activity obtained here will be referred to as a specified biological activity hereinafter.

In Step 601, the search module 109 obtains one or more chemical compounds recorded on the exemplar table 300 whose biological activities match the specified biological activity as the specified chemical compounds. The meaning of "match" may be defined by those skilled in the art as needed, and for example this includes a case wherein the biological activity of a chemical compound is the same as the specified biological activity. If biological activities of a plurality of chemical compounds match the specified biological activity, a plurality of specified chemical compounds will be resulted. Hereinafter, a case wherein there are a plurality of specified chemical compounds will be explained.

The search module 109 calculates the feature vectors distance between each specified chemical compound and each chemical compound in the search table 400 (Step 602). Let the feature vectors of the specified chemical compounds be X, Y and the feature vectors of the chemical compounds in the search table 400 be A, B, C, then feature vectors distances X-A, X-B, X-C, Y-A, Y-B, Y-C are calculated. That is, the number of the feature vectors distances calculated is the number of the specified chemical compounds multiplied by the number of chemical compounds recorded on the search table. The specific calculation method for the feature vectors distances may be similar to Step 502 of FIG. 5.

The search module 109 sorts the search result and obtains similar chemical compounds (Step 603) in a manner similar to the process of FIG. 5 and outputs the search result to the GUI 102 (Step 604). The GUI 102 receives and displays this. Here, in the example of FIG. 6, a plurality of feature vectors distances are calculated for one similar chemical compound, so the GUI 102 will display a same similar chemical compounds for multiple times.

Figure 7:
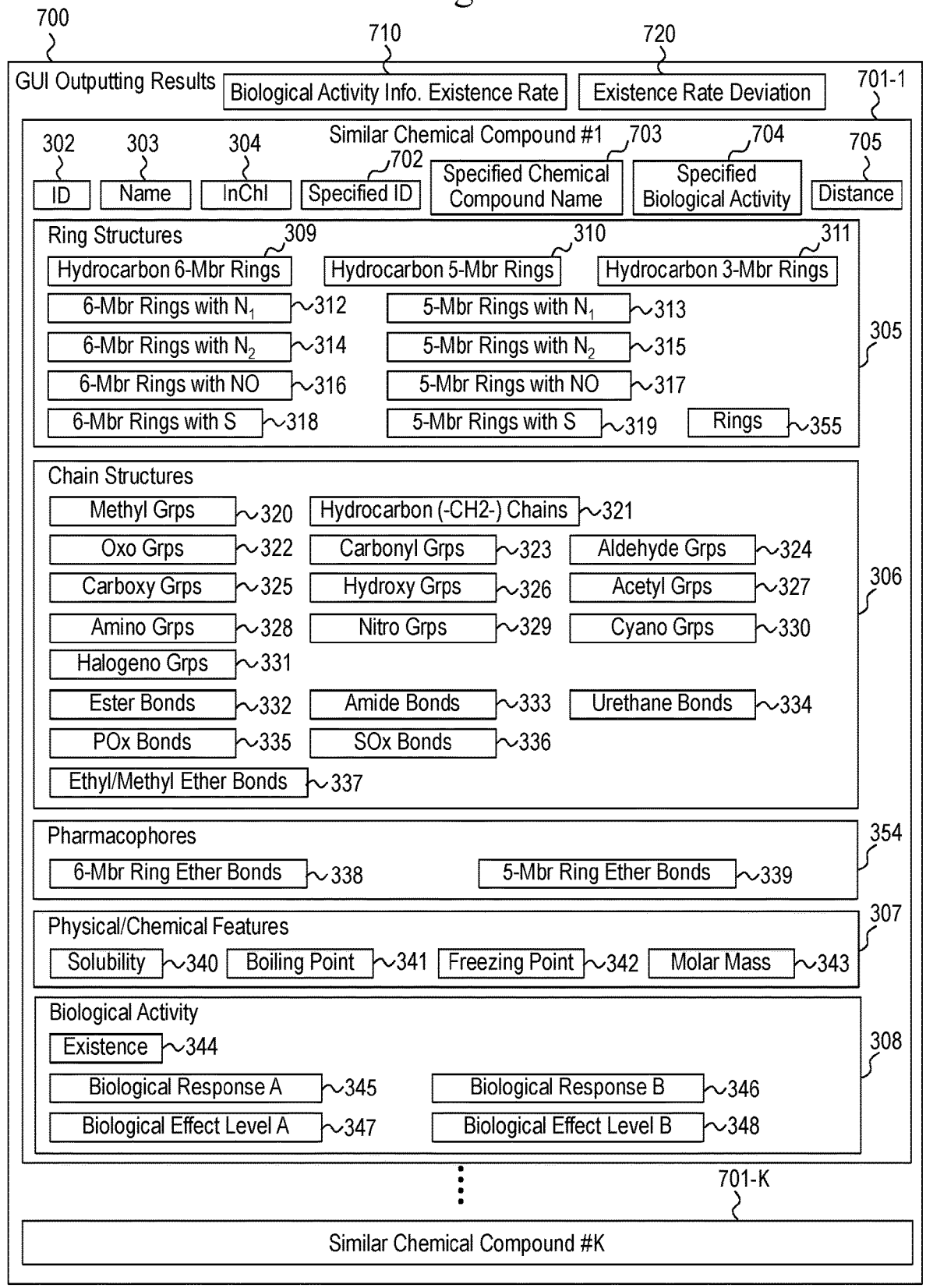
FIG. 7 is a GUI for searching and outputting similar chemical compounds from the search table based on feature vectors distances to user-specified chemical compounds or chemical compounds having a user-specified biological activity in the first embodiment.

FIG. 7 is a GUI 700 for searching and displaying similar chemical compounds from the search table 400 based on feature vectors distances to the specified chemical compounds or to the chemical compounds having the specified biological activity in the first embodiment. This GUI 700 may be a part of the GUI 102 of FIG. 1.

The GUI 700 displays the similar chemical compounds. In order for this, the GUI 700 includes an entry 701 for each similar chemical compound in a manner similar to the search table 400. The entry 701 includes the ID number 302 identifying the chemical compound, the chemical compound name 303, the IhChI formula 304, the ring structure information 305, the chain structure information 306, the pharmacophore information 354, the physical/chemical feature information 307 and the biological activity information 308. The GUI 700 displays information regarding a plurality (for example K) of chemical compounds and the entries 701 of respective chemical compounds are shown as entries 701-1 to 701-K in FIG. 7.

Further, the entry 701 includes an ID number 702 of the specified chemical compound and a chemical compound name 703 of the specified chemical compound. Also, the entry 701 may include a specified biological activity 704. Further, the entry 701 includes a feature vectors distance 705 between the similar chemical compound and the specified chemical compound.

By using the GUI 700 displaying the result outputted by the search module 109 of the search system 100, the user can search chemical compounds having a high similarity in terms of both the structural features and the physical/chemical features with a high accuracy.

Further, the GUI 700 may display a biological activity information existence rate 710 for the similar chemical compound displayed in the search result and an existence rate deviation 720. In order for this, the search module 109 may calculate a ratio of the similar chemical compounds for which information representing any biological activity is recorded to all the similar chemical compounds (the ratio corresponds to the biological activity information existence rate 710; hereinafter referred to as "similar chemical compound biological activity information existence rate"). Whether or not the information representing the biological activity is recorded may be determined based on the existence flag 344 regarding the chemical compound. The GUI 700 may display an average value and a predicted value of the biological effect level and a total number of the biological responses for each type, as a summary of biological activity information of the displayed similar chemical compounds.

Also, the search module 109 may calculate a ratio of the chemical compounds recorded on the search table 400 for which any information representing biological activity is recorded to all the chemical compounds recorded on the search table 400 (hereinafter referred to as "total biological activity information existence rate").

Further, the search module 109 may calculate the existence rate deviation 720 based on the similar chemical compound biological activity information existence rate and the total biological activity information existence rate. The existence rate deviation 720 may for example be calculated as a ratio of these two values. As a specific example, this is calculated as the similar chemical compound biological activity information existence rate divided by the total biological activity information existence rate. The GUI 700 receives and displays these values from the search module 109.

The similar chemical compound biological activity information existence rate can be considered to represent a ratio of the similar chemical compound for which some human existed in the past who desired to evaluate their biological activity, and the existence rate deviation is an indication fix how many of thinking patterns or behavior patterns of the humans in the past are reproduced in the search result.

Also, the search module 109 may calculate an average of the document scores (average document score) for all the similar chemical compounds and the GUI 700 may receive and display the average document score. In this manner, biological activities not registered on the general chemical compound database 103 can also be utilized. Note that the document score can be used as an indication of prospect.

Figure 8:
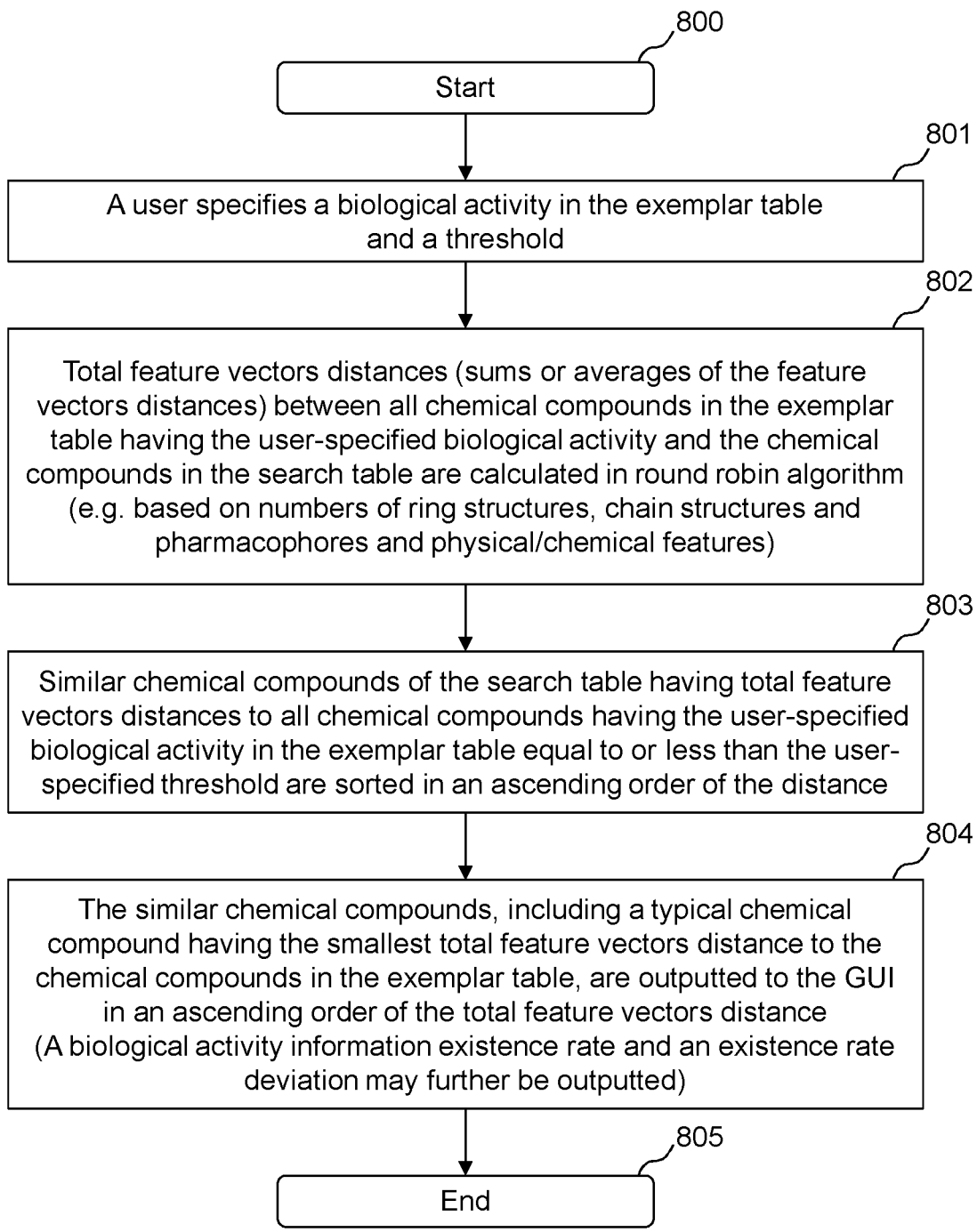
FIG. 8 is a flowchart showing a process for searching and outputting a typical chemical compound from the search table based on a sum of feature vectors distances to all chemical compounds having a user-specified biological activity in the first embodiment.

FIG. 8 is a flowchart showing a process for searching and outputting a typical chemical compound from the search table 400 based on a sum of feature vectors distances to all chemical compounds having the specified biological activity in the first embodiment.

The search module 109, upon receiving the search command 126 from the user 106, starts the process of FIG. 8 (Step 800) and ends the process (Step 805) after outputting a search result 125 to the GUI 102.

In regard to the process of FIG. 8, the user 106 uses the search command 126 in order to specify one specified biological activity and a threshold for the feature vectors distance (Step 801). The search module 109 obtains the specified biological activity and the threshold via the search command 126.

In Step 801, the search module 109 obtains one or more chemical compounds whose biological activities match the specified biological activity among the chemical compounds recorded on the exemplar table 300 as the specified chemical compounds. If biological activities of a plurality of chemical compounds match the specified biological activity, a plurality of specified chemical compounds are resulted. A case wherein a plurality of specified chemical compounds are resulted is explained below.

The search module 109 calculates a total feature vectors distance between each specified chemical compound and each chemical compound of the search table 400 (Step 802). In Step 802, first, the search module 109 calculates feature vectors distances X-A, X-B, X-C, Y-A, Y-C wherein the feature vectors of the specified chemical compounds are X, Y and the feature vectors of the chemical compounds of the search table 400 are A, B, C. The specific calculation method for the feature vectors distances may be similar to Step 502 of FIG. 5.

In Step 802, next, the search module 109 calculates a sum of the feature vectors distances for each chemical compound of the search table 400. For example, in the above example, if the feature vector of a chemical compound is A, the sum of the feature vectors distances will be the sum of X-A and Y-A. The total feature vectors distance may be this sum or may be the sum divided by the number of the specified chemical compounds (i.e. average).

Note that the total feature vectors distance may be calculated by concatenating vectors. For example, first, vectors X and are concatenated to obtain a concatenated vector XY. The dimension of the concatenated vector XY is equal to the sum of the dimension of vector X and the dimension of vector Y (i.e. two times the dimension of the vector X). The former half of the elements in the concatenated vector XY are identical to the elements of vector X and the latter half of the elements in the concatenated vector XY are identical to the elements of vector Y.

Next, vector A is concatenated with vector A per se to obtain a concatenated vector AA. Then, the concatenated vectors distance XY-AA is calculated between the concatenated vector XY and the concatenated vector A. Note that the concatenated vectors distance XY-AA is equal to the sum of the feature vectors distances X-A and Y-A. The total feature vectors distance may be this concatenated vectors distance or may be the concatenated vectors distance divided by the number of the specified chemical compounds (i.e. average).

The search module 109 obtains similar chemical compounds by sorting the search result, in a manner similar to the process of FIG. 5 (Step 803). Here, the search module 109 obtains a similar chemical compound for which the total feature vectors distance (e.g. the sum or average of the feature vectors distances) to the specified chemical compounds is smallest as a typical chemical compound. Then, the search module 109 outputs information regarding the similar chemical compounds and the typical chemical compound to the GUI 102 (Step 804).

The GUI 102 receives and displays this. The GUI 102 may display the similar chemical compounds in an ascending order of the total feature vectors distance. Also, the GUI 102 may display information for identifying the typical chemical compound upon displaying the similar chemical compounds. For example, if a similar chemical compound is the typical chemical compound, a text such as "typical structure" may be displayed in the vicinity of the name of the similar chemical compound.

Figure 9:
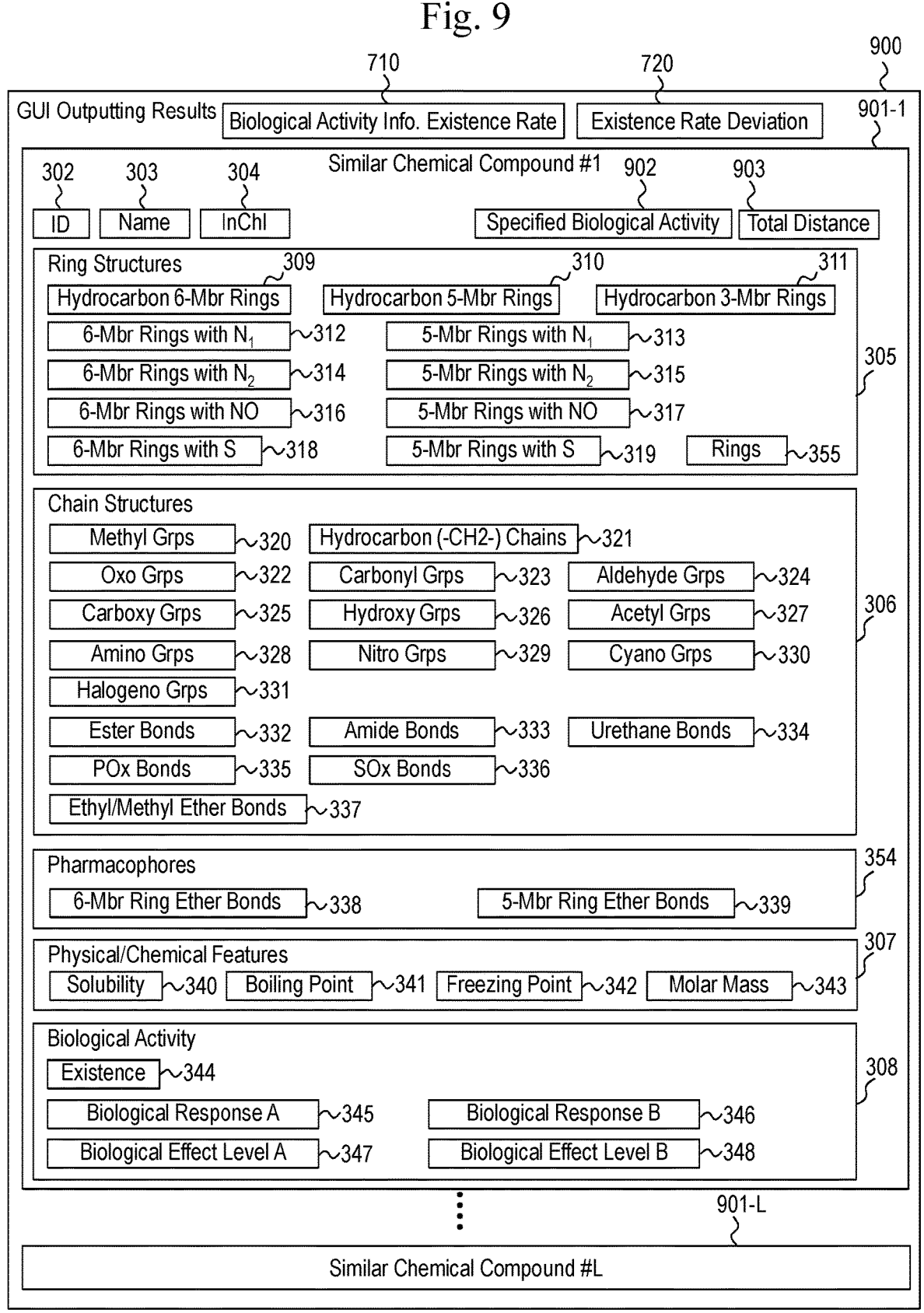
FIG. 9 is a GUI for searching and outputting a typical compound from the search table based on a sum of feature vectors distances to all chemical compounds having a user-specified biological activity in the first embodiment.

FIG. 9 is a GUI 900 for searching and outputting the typical compound from the search table 400 based on a sum of feature vectors distances to all chemical compounds having the specified biological activity in the first embodiment. The GUI 900 may for example be a part of the GUI 102 of FIG. 1. The GUI 900 displays information regarding plurality (for example L) of chemical compounds and the entries 901 of respective chemical compounds are shown as entries 901-1 to 901-1, in FIG. 9.

Content of the GUI 900 may include the content same as that of the GUI 700 shown in FIG. 7. Also, as explained above, the GUI 900 may display information for identifying the typical chemical compound upon displaying the similar chemical compounds. For example, if a similar chemical compound is the typical chemical compound, a text such as "typical structure" may be displayed in the vicinity of the name of the similar chemical compound. Further, the GUI 900 may display the specified biological activity 902 and the total feature vectors distance 903 for each similar chemical compound.

Figure 10:
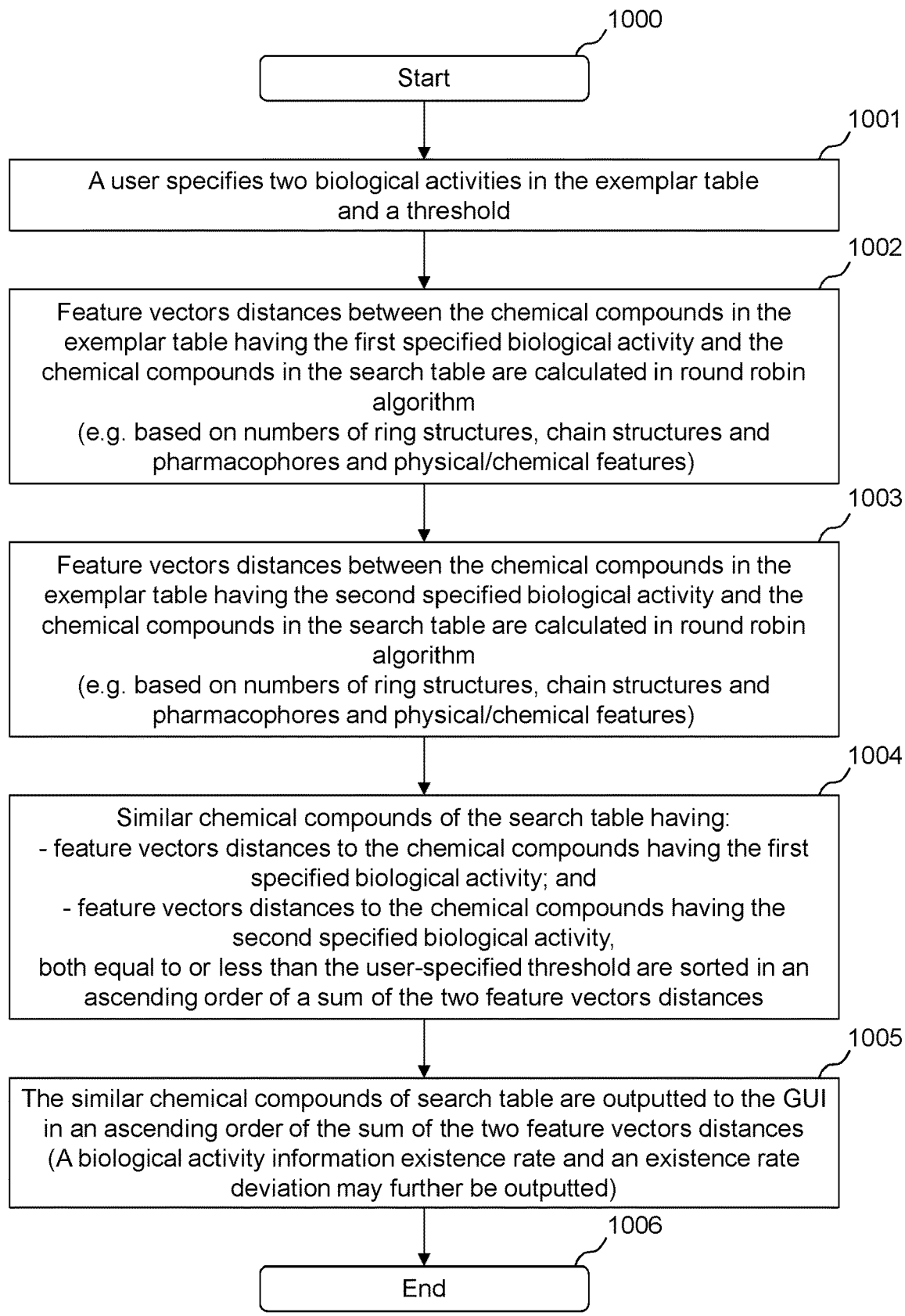
FIG. 10 is a flowchart showing a process for searching and outputting chemical compounds, from the search table, similar to both chemical compounds having a first user-specified biological activity and chemical compounds having a second user-specified biological activity in the first embodiment.

FIG. 10 is a flowchart showing a process for searching and outputting chemical compounds from the search table 400 similar to both chemical compounds having a first user-specified biological activity and chemical compounds having a second user-specified biological activity in the first embodiment.

The search module 109, upon receiving the search command 126 from the user 106, starts the process of FIG. 10 (Step 1000) and ends the process (Step 1006) after outputting a search result 125 to the GUI 102.

In regard to the process of FIG. 10, the user 106 uses the search command 126 in order to specify a plurality (two in the example of FIG. 10) of biological activities and a threshold for the feature vectors distance (Step 1001). The search module 109 obtains a first specified biological activity, a second specified biological activity and the threshold via the search command 126.

In Step 1001, the search module 109 obtains one or more chemical compounds whose biological activities match the first specified biological activity among the chemical compounds recorded on the exemplar table 300. The chemical compounds obtained here will be referred to as first specified chemical compounds hereinafter. If biological activities of a plurality of chemical compounds match the first specified biological activities, a plurality of first specified chemical compounds are resulted.

Also, in Step 1001, the search module 109 obtains one or more chemical compounds whose biological activities match the second specified biological activity among the chemical compounds recorded on the exemplar table 300. The chemical compounds obtained here will be referred to as second specified chemical compounds hereinafter. If biological activities of a plurality of chemical compounds match the second specified biological activities, there are a plurality of second specified chemical compounds.

The search module 109 calculates the feature vectors distance between each first specified chemical compound and each chemical compound of the search table 400 (Step 1002). The specific calculation method for calculating the feature vectors distances may be similar to Step 502 of FIG. 5.

Also, the search module 109 calculates the feature vectors distance between each second specified chemical compound and each chemical compound of the search table 400 (Step 1003). The specific calculation method for the feature vectors distances may be similar to Step 502 of FIG. 5.

Next, the search module 109 sorts the search result (Step 1004). Here, the search module 109 sorts the chemical compounds of the search table 400 for which the feature vectors distances to the two specified chemical compounds are both equal to or less than the user-specified threshold in an ascending order of the sum (or the average, same hereinafter) of the two feature vectors distances (Step 1004).

That is, the search module 109 obtains the chemical compounds, among the similar chemical compounds, for which the sum of feature vectors distances to the first specified chemical compounds are equal to or less than the threshold and the sum of feature vectors distances to the second specified chemical compounds are equal to or less than the threshold. The chemical compounds obtained here will be referred to as multiple biological activity chemical compounds hereinafter. It can be said that the multiple biological activity chemical compounds are common similar chemical compounds which are similar to both of two chemical compounds matching two corresponding types of biological activity.

The search module 109 outputs the multiple biological activity chemical compounds in an ascending order of a total of the sums of the feature vectors distances (that is, a total of the sum of the feature vector distances to the first specified chemical compounds and the sum of the feature vectors distances to the second specified chemical compounds) to the GUI 102 (Step 1005). The multiple biological activity chemical compounds are candidates for chemical compounds having both the first and second biological activities specified by the user at the same time.

The GUI receives and displays this. The GUI 102 may display the similar chemical compounds including the multiple biological activity chemical compounds in an ascending order of the total of the sums of the feature vectors distances. Also, the GUI 102 may display information for identifying the multiple biological activity chemical compounds upon displaying the similar chemical compounds. For example, if a similar chemical compound is a multiple biological activity chemical compound, a text such as "matching all biological activities" may be displayed in the vicinity of the name of the similar chemical compound.

Figure 11:
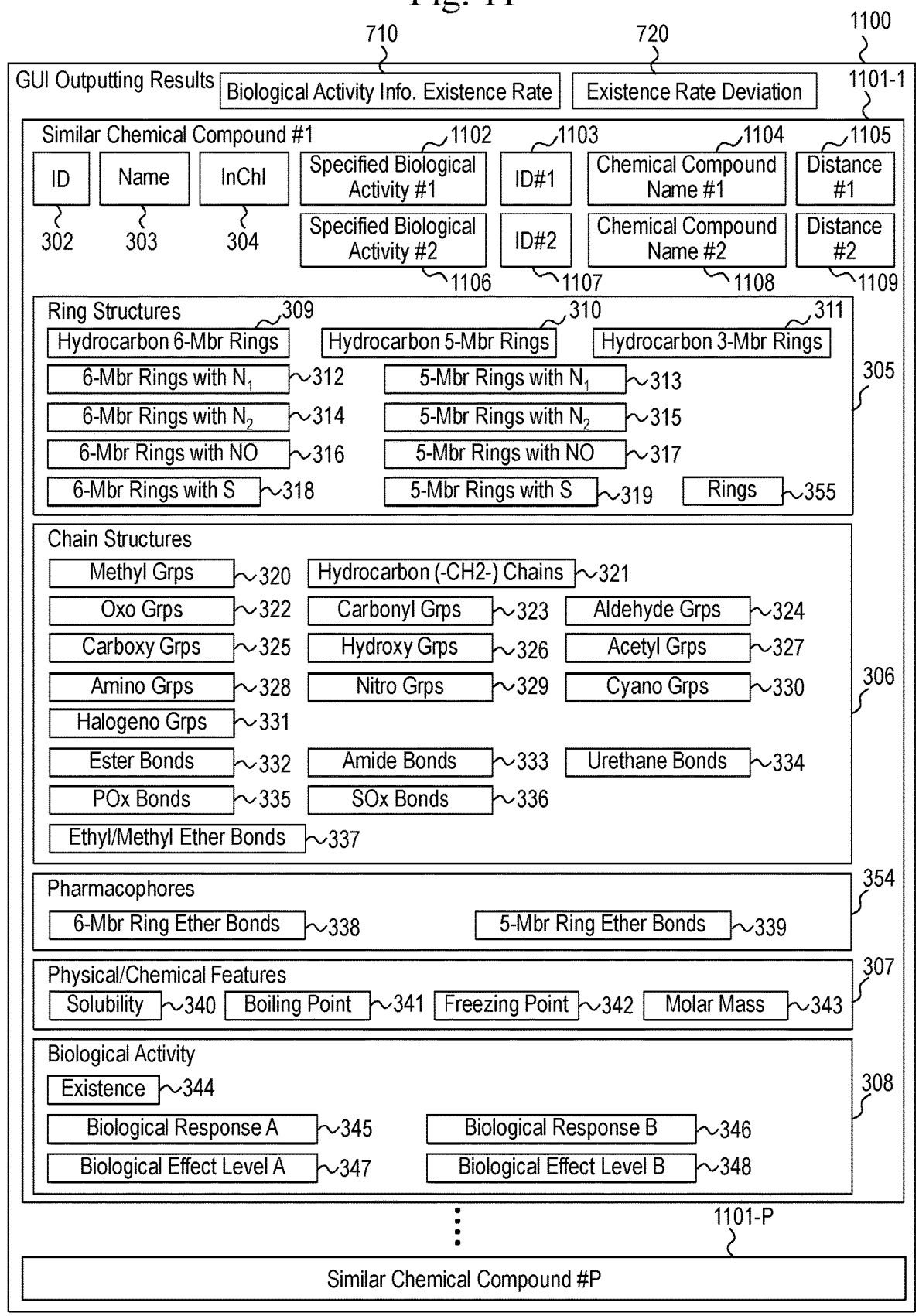
FIG. 11 is a GUI for outputting chemical compounds similar to both chemical compounds having a first user-specified biological activity and chemical compounds having a second user-specified biological activity in the first embodiment.

FIG. 11 is a GUI 1100 for searching and outputting chemical compounds similar to both the first and second specified chemical compounds from the search table 400 in the first embodiment. The GUI 1100 may for example be a part of the GUI 102 of FIG. 1. The GUI 1100 displays information regarding plurality (for example P) of chemical compounds and the entries 1101 of respective chemical compounds are shown as entries 1101-1 to 1101-P in FIG. 11.

Content of the GUI 1100 may include the content same as that of the GUI 700 shown in FIG. 7. Also, as explained above, the GUI 1100 may display information for identifying the multiple biological activity chemical compounds upon displaying the similar chemical compounds. For example, if a similar chemical compound is a multiple biological activity chemical compound, a text such as "matching all biological activities" may be displayed in the vicinity of the name of the similar chemical compound.

Note that the GUI 1100 may display, as information regarding the first specified biological activity, a biological activity 1102, an ID number 1103 for identifying the biological activity, a name 1104 (or a list of names) of the chemical compound having the biological activity and the total feature vectors distance 1105. In a similar manner, the GUI 1100 may display, as information regarding the second specified biological activity, a biological activity 1106, an ID number 1107 for identifying the biological activity, a name 1108 (or a list of names) of the chemical compound having the biological activity and the total feature vectors distance 1109.

Figure 12:
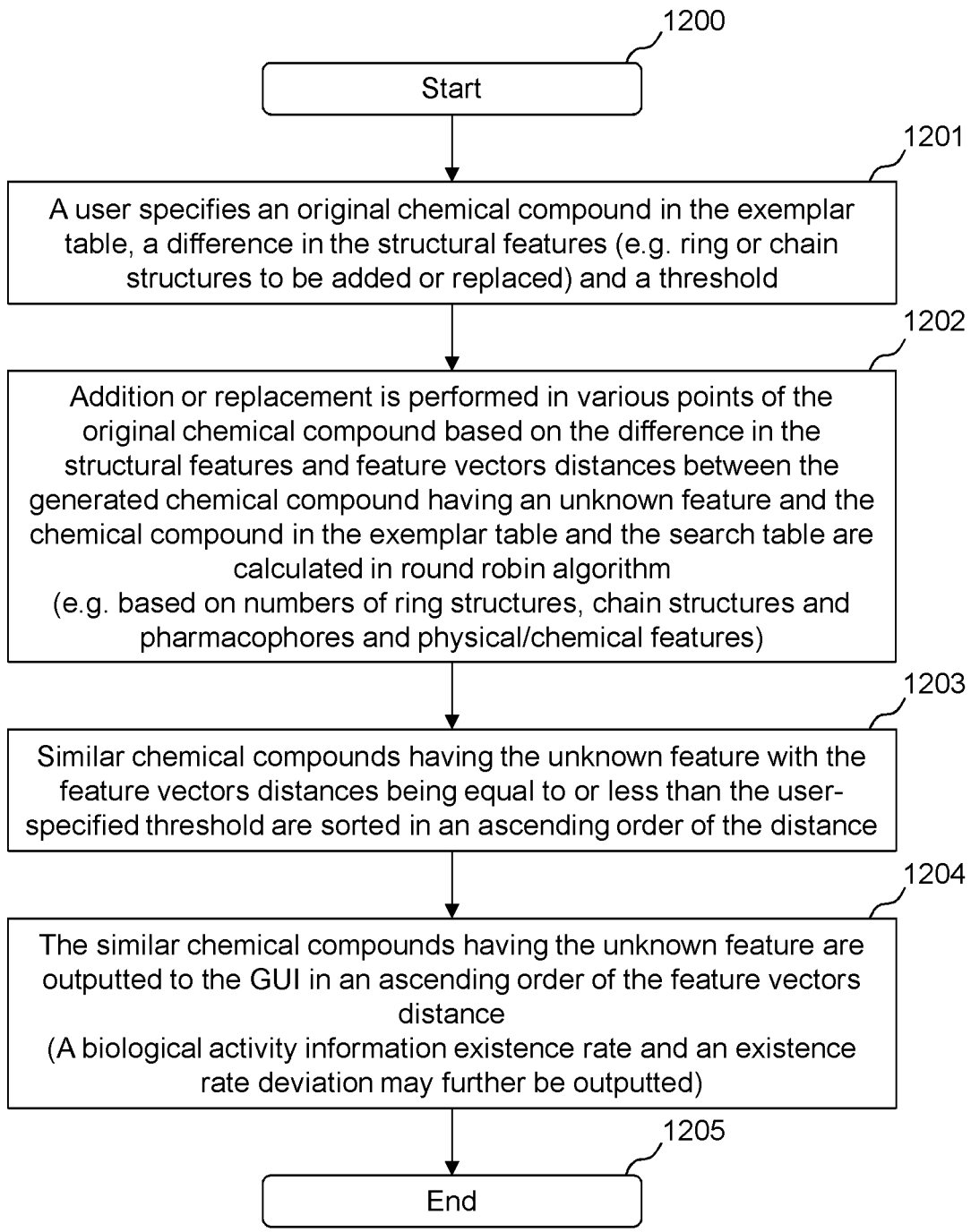
FIG. 12 is a flowchart showing a process for searching and outputting similar chemical compounds having some biological activity with an unknown feature from the search table or the exemplar table based on feature vectors distances to a specified chemical compound having an unknown new feature wherein a user-specified structure is added or replaced with respect to a feature vector of a user-specified original chemical compound in the first embodiment.

FIG. 12 is a flowchart showing a process for searching and outputting similar chemical compounds having some biological activity with an unknown feature from the exemplar table 300 or the search table 400 based on the feature vectors distances to a specified chemical compound having an unknown feature wherein a user-specified structure is added or replaced with respect to a feature vector of an original chemical compound in the first embodiment.

The search module 109, upon receiving the search command 126 from the user 106, starts the process of FIG. 12 (Step 1200) and ends the process (Step 1205) after outputting a search result 125 to the GUI 102.

In regard to the process of FIG. 12, the user 106 uses the search command 126 in order to specify one chemical compound recorded on the exemplar table 300 (referred to as "original chemical compound" hereinafter), information representing a difference in the structural features and a threshold for the feature vectors distance (Step 1201). The search module 109 obtains the chemical compound recorded on the exemplar table 300, the information representing the difference in the structural features and a threshold for the feature vectors distance via the search command 126.

Next, the search module 109 calculates the feature vectors distance between a specified chemical compound, which is an unknown chemical compound based on the difference in the structural features, and each chemical compound of the search table 400 (Step 1202). In Step 1202, the search module 109 obtains one or more specified chemical compounds by applying the difference in the structural features to the structural features of the original chemical compound specified in Step 1201.

The difference in the structural features may be represented by addition or replacement. Addition means for example adding a user-specified structure in a user-specified point of the original chemical compound. Replacement means for example replacing a structure in a user-specified point of the original chemical compound with another user-specified structure. Specific examples will be explained later using FIG. 13. Addition or replacement allows the specified chemical compound to be a new chemical compound (possibly having an unknown feature or structure).

In Step 1202, next, the search module 109 obtains feature vectors for thus generated specified chemical compound, the chemical compounds recorded on the exemplar table 300 and the chemical compounds recorded on the search table 400. Note that, unlike the process of FIG. 5, the chemical compounds recorded on the exemplar table 300 are also searched in the process of FIG. 12 because the specified chemical compound is different from any chemical compounds recorded on the exemplar table 300 (however, in an alternative example, the exemplar table 300 may be excluded from the search).

In Step 1202, next, the search module 109 calculates the feature vectors distance between the feature vector of the specified chemical compound and each chemical compound recorded on the exemplar table 300. Also, the search module 109 calculates the feature vectors distance between the feature vector of the specified chemical compound and each chemical compound recorded on the search table 400. The specific calculation method for the feature vectors distances may be similar to Step 502 of FIG. 5.

The search module 109 sorts the search result (Step 1203). In Step 1203, the search module 109 first obtains at least one of the chemical compounds recorded on the exemplar table 300 or the chemical compounds recorded on the search table 400 in response to the feature vectors distances. In the first embodiment, it obtains the chemical compounds of the exemplar table 300 or the search table 400 for which the features vectors distances to the specified chemical compound are equal to or less than a user-specified threshold (obtains the similar chemical compounds) and sorts them in an ascending order of the feature vectors distance.

The search module 109 outputs the search result to the GUI 102 in a manner similar to the process of FIG. 5 and GUI 102 receives and displays this.

Figure 13:
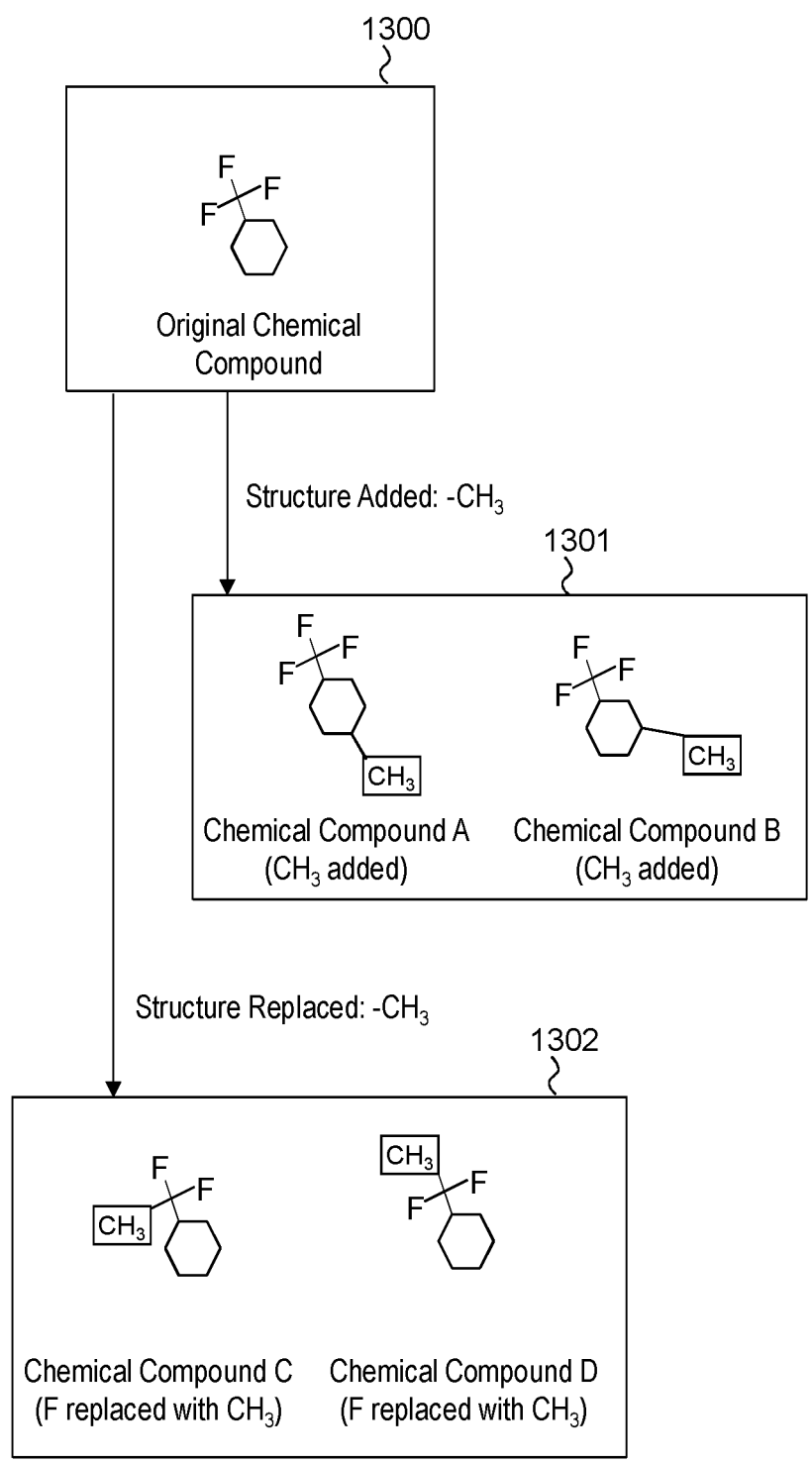
FIG. 13 is a diagram explaining a process for creating a chemical compound having an unknown new feature wherein a user-specified structure is added or replaced in various points of a user-specified chemical compound in the first embodiment.

FIG. 13 is a diagram explaining a process for creating a chemical compound having an unknown new feature wherein a user-specified structure is added or replaced in various points of a user-specified chemical compound in the first embodiment.

Let a user-specified chemical compound (i.e. an original chemical compound for which addition or replacement is to be made) be the chemical compound 1300. Also, in an example, adding a methyl group in a meta position of the chemical compound 1300 and adding a methyl group in a para position of the chemical compound 1300 are specified as a difference in the structural features. In this case, two specified chemical compounds 1301 are generated including chemical compounds A and B shown in FIG. 13. (Note that addition of a methyl group or the like may actually represent replacement of a hydrogen atom with it.)

In an another example, replacing one of fluorine atoms in the chemical compound 1300 with a methyl group is specified as the difference in the structural features. In this case, two specified chemical compounds 1302 including chemical compounds C and D shown in FIG. 13 are generated. (Note that FIG. 13 shows the chemical compounds C and D as different chemical compounds for facilitating explanation).

FIG. 13 shows examples of addition and replacement using a methyl group, but a hydro group or other structures may be added or replaced.

Content displayed on the GUI 102 based on the process of FIG. 12 may be the same as the GUI 700 of FIG. 7. Also, the search module 109 may output information regarding the specified chemical compound in addition to the information regarding the similar chemical compounds to the GUI 102, and the GUI 102 may display the information regarding the specified chemical compound. Such an example is shown in FIG. 14.

Figure 14:
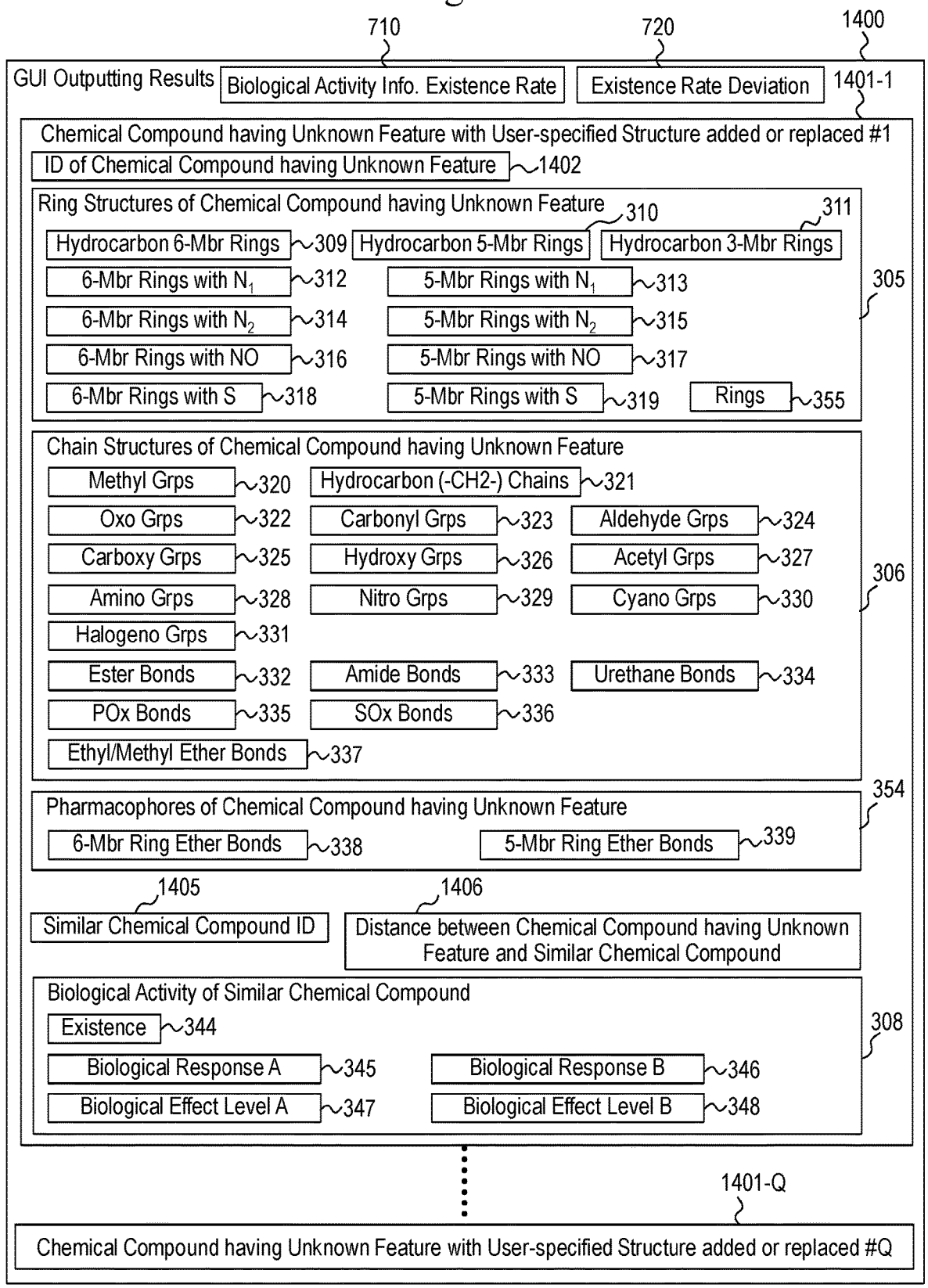
FIG. 14 is a GUI for outputting a biological activity information existence rate and an existence rate deviation for a chemical compound having an unknown new feature wherein a user-specified structure is added or replaced with respect to a user-specified chemical compound in the first embodiment.

FIG. 14 is a GUI 1400 for outputting a biological activity information existence rate and an existence rate deviation for an unknown chemical compound (the specified chemical compound) wherein a user-specified structure is added or replaced with respect to the original chemical compound in the first embodiment. The GUI 1400 may for example be a part of the GUI 102 of FIG. 1. The GUI 1400 displays information regarding a plurality (for example Q) of chemical compounds and the entries 1401 of respective chemical compounds are shown as entries 1401-1 to 1401-Q in FIG. 14.

The GUI 1400 may include an ID number 1402 of the specified chemical compound. Also, the GUI 1400 may display, for each specified chemical compound, an ID number 1405 (or a list of ID numbers) of similar chemical compound related to the specified chemical compound, the feature vectors distance 1406 (or a list of the feature vectors distances) between the specified chemical compound and the similar chemical compound, etc.

Figure 15:
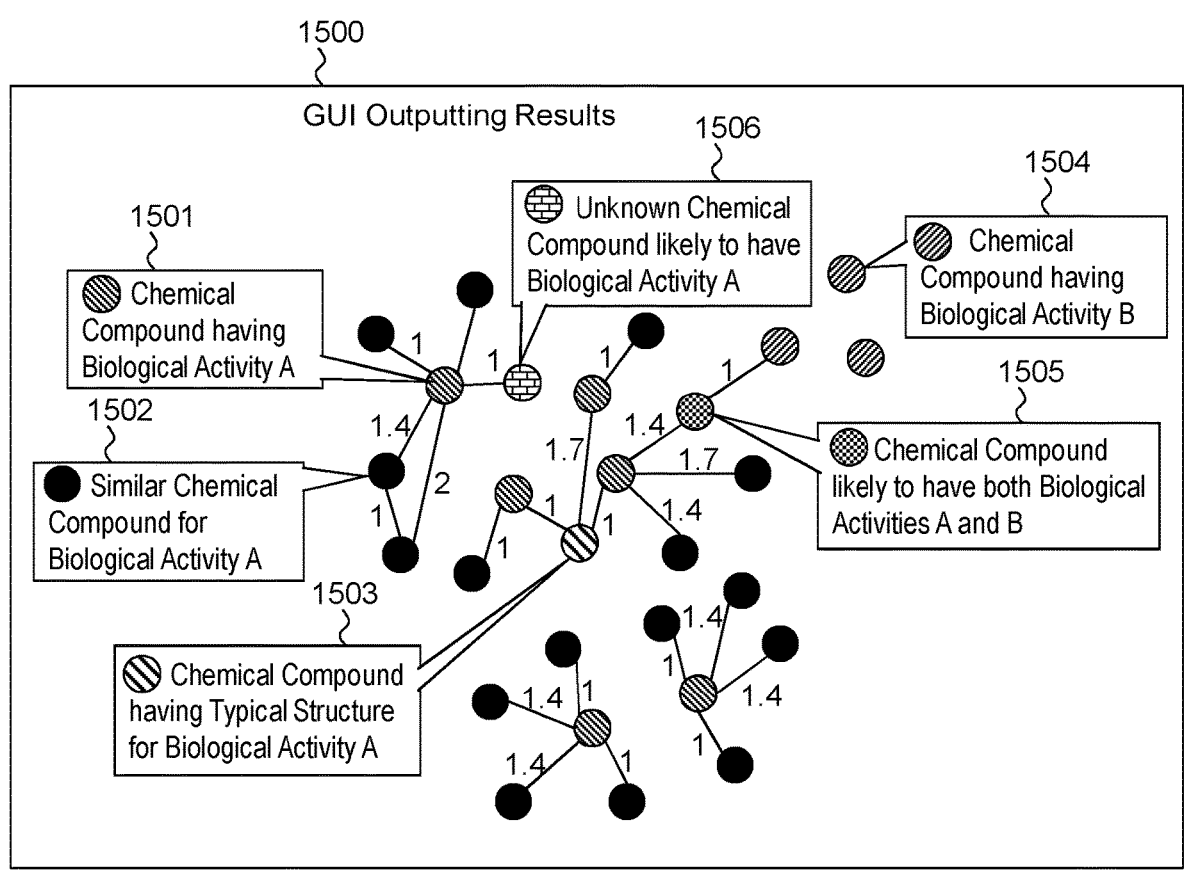
FIG. 15 is a GUI for representing chemical compounds as nodes and feature vectors distances as lengths or thicknesses of the lines between the nodes in the first embodiment.

FIG. 15 is a GUI 1500 for representing chemical compounds as nodes and feature vectors distances as lengths or thicknesses of the lines between the nodes in the first embodiment. The GUI 1500 shows parts of displayed examples corresponding to the processes of FIGS. 5, 6, 8, 10, 12 in a collective manner, and the entire portion of the FIG. 15 may not correspond to any specific process.

GUI 1500 may display a graph screen. The graph screen displays the chemical compounds as nodes. For example, the graph screen displays first specified chemical compounds 1501 of the exemplar table 300 comprising the first specified biological activity A and second specified chemical compounds 1504 of the exemplar table 300 comprising the second specified biological activity B. The graph screen also displays similar chemical compounds 1502 (for which the specified biological activity is the biological activity A) outputted in the process of FIG. 6 and displayed on the GUI 700 of FIG. 7. The graph screen also displays a typical chemical compound 1503 (for which the specified biological activity is the biological activity A) outputted in the process of FIG. 8 and displayed on the GUI 900 of FIG. 9. The graph screen also displays a multiple biological activity chemical compound 1505 (for which the first specified biological activity is the biological activity A and the second specified biological activity is the biological activity 4) outputted in the process of FIG. 10 and displayed on the GUI 1100 of FIG. 11. The graph screen also displays a specified or similar chemical compound 1506 having an unknown feature outputted in the process of FIG. 12 and displayed on the GUI 1400 of FIG. 14.

In the graph screen, the nodes may be displayed in different colors in response to their types. For example, a specified chemical compound and a similar chemical compound may be displayed as nodes of respectively different colors. Specified chemical compounds related to respectively different specified biological activities may be displayed as nodes of respectively different colors. A typical chemical compound among the similar chemical compounds may be displayed as a node of a color different from the other similar chemical compounds. A multiple biological activity chemical compound among the similar chemical compounds may be displayed as a node of a color different from the other similar chemical compounds. A chemical compounds having an unknown feature (e.g. a chemical compound generated by addition or replacement) may be displayed as a node of a color different from the other chemical compound.

Differentiating the colors of the nodes in this way facilitates the user to understand meaning of each node and grasp the relationships among the nodes.

In the graph screen, lines connecting the nodes may be displayed. In this case, a length or a thickness of the line connecting the nodes (e.g. a line connecting the node of a specified chemical compound and the nodes of the similar chemical compounds) may be determined based on their feature vectors distances. In this manner, the relationships among the nodes can be grasped more easily.

FIG. 16 is a GUI 1600 for inputting, by the user, a threshold for feature vectors distance, information for selecting a search table to be used, an original chemical compound, weight values for masking or weighting feature amounts, and a difference in structural features for creating unknown feature amounts in the first embodiment.

The GUI 1600 includes any or all of the items below:
a textbox fix specifying a threshold for extracting similar chemical compounds having a single biological activity;
a textbox for specifying a threshold for extracting similar chemical compounds having all of a plurality of biological activities;
radio buttons for specifying a search table to be used;
a textbox for specifying weight values for masking or weighting each element (feature amount) of the feature vectors;
a textbox for inputting difference in the structural features for creating unknown feature amounts;
a group of check boxes for specifying an exemplar table chemical compound Which is a chemical compound recorded on the exemplar table 300 and has a first specified biological activity (this may be used to specify a specified chemical compound directly); and
a group of check boxes for specifying an exemplar table chemical compound which is a chemical compound recorded on the exemplar table 300 and has a second specified biological activity (this may be used to specify a specified chemical compound directly).

In the textbox for specifying the weight values, a sequence including 0 or positive numerical values may be inputted. The numerical values correspond to respective feature amounts. Upon applying the weight values in calculation of the feature vectors distances, for example, at first, a product of two corresponding feature amounts is calculated, and then, the product is multiplied by a corresponding weight value. A corresponding relationship between an order of the feature amounts and an order of the weight values may be defined beforehand. For example, the first numerical value corresponds to the number of six-membered hydrocarbon rings, the second numerical value corresponds to the number of five-membered hydrocarbon rings and the third numerical value corresponds to the number of three-membered hydrocarbon rings.

A feature amount which is not desired to be used in calculation of the feature vectors distances can be masked by setting the corresponding numerical value to 0. Also, as to a feature amount which is desired to be significant in calculation of the feature vectors distances, contribution to the distances can be increased by setting the corresponding numerical value larger.

The range of the weight values may be determined in any manner, and for example be a range including an interval from 0 to 2, inclusive. In this case, the search module 109 can change the weight values of respective elements in the feature vectors within a range including the interval from 0 to 2 upon calculating the feature vectors distances.

In the text box for inputting difference in the structural features, information representing the difference in the structural features may be inputted as a sequence including numerical values having positive or negative signs. That is, the search module 109 obtains the information representing the difference in the structural features as the sequence including numerical values having positive or negative signs. Using this format facilitates the user to specify the difference in the structural features.

The corresponding relationship between an order of the structural features and an order of the inputted numerical values may be defined beforehand. For example, if the third numerical value is 5 (i.e. +5) as in the example of FIG. 16, the number of three-membered hydrocarbon rings is increased by 5 in the original chemical compound. Also, if the fifth numerical value is −4, the number of five-membered rings including exactly one nitrogen atom is decreased by 4 in the original compound. Thus the specified chemical compound is determined.

Figure 17:
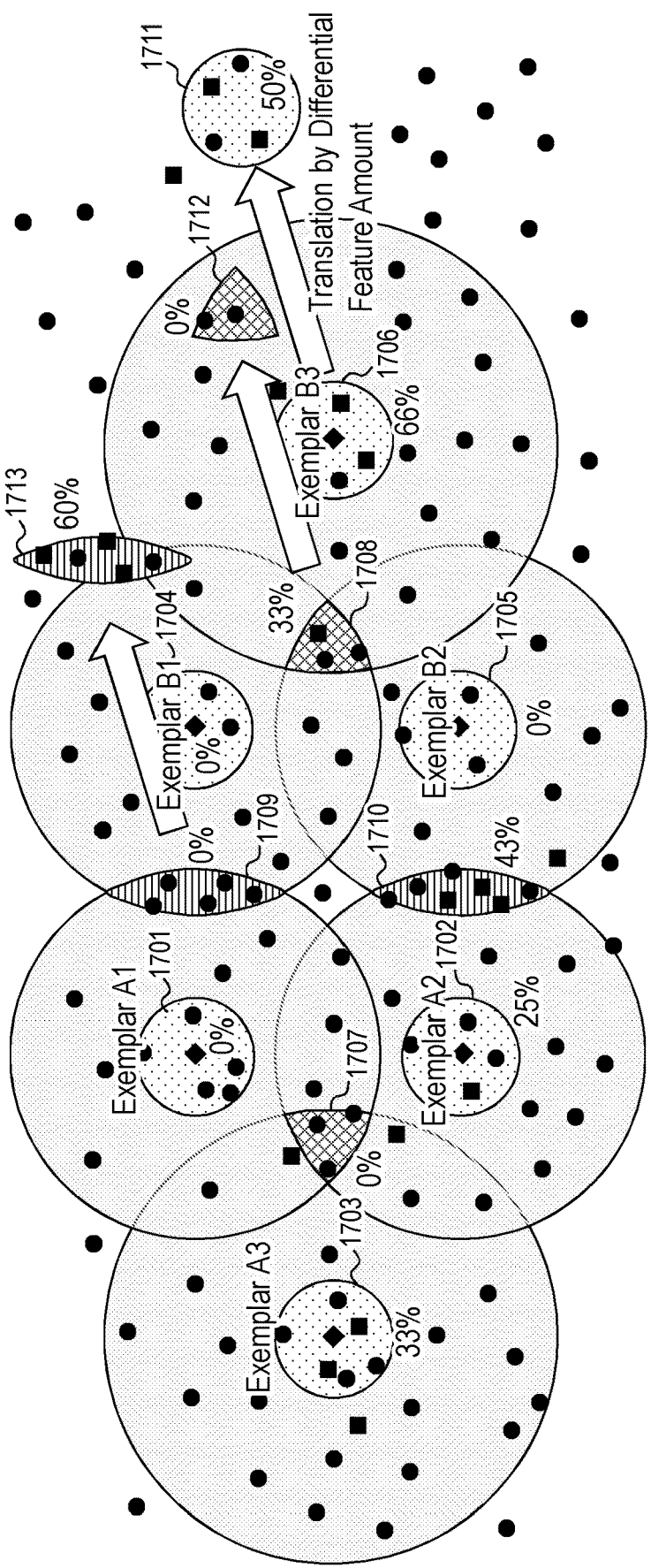
FIG. 17 is a diagram for explaining similar chemical compounds, typical chemical compounds, common similar chemical compounds and biological activity information existence rates in the first embodiment.

FIG. 17 is a diagram for explaining similar chemical compounds, typical chemical compounds, multiple biological activity chemical compounds and biological activity information existence rates in the first embodiment. This example shows hopeful chemical compound region spaces (including the specified chemical compounds, the similar chemical compounds, the typical chemical compounds and the multiple biological activity chemical compounds) in a feature vector space and biological activity information existence rates in respective spaces.

A dimension of the feature vector changes in response to the number of items of the feature amounts, so the feature vector space may have any of one to three dimensions or more. If the feature vector space is in three or more dimensions, the feature vector space may be displayed by being mapped into a lower dimension. FIG. 17 shows an example wherein the space is mapped in two dimensions.

Diamond-shaped points represent coordinates of feature vectors of chemical compounds included in the exemplar table 300 (specified chemical compounds). Cocentric circles centering the diamond-shaped points (the exemplars A1-A3 and B1-B3) represent respective hopeful chemical compound spaces 1701-1706 including respective similar chemical compounds.

The hopeful chemical compound spaces 1701-1706 include coordinates of feature vectors of similar chemical compounds of the search table 400 represented by circular points and square points. The circular points represent coordinates of feature vectors of similar chemical compounds for which there is no biological activity information whereas the square points represent coordinates of feature vectors of similar chemical compounds for which there is biological activity information.

The hopeful chemical compound spaces 1701-1706 includes, respectively, 5, 3, 4, 2, 3, 1 similar chemical compounds for which there is no biological activity information (circular points) and 0,1,2,0,0,2 similar chemical compounds for which there is biological activity information (square points). Accordingly, respective biological activity information existence rates are 0%, 25%, 33%, 0%, 0%, 66%.

The exemplars A1-A3 all match the specified biological activity A. The hopeful chemical compound space 1707 is a region with small distances from all of the coordinates of the three exemplar feature vectors and includes coordinates of feature vectors of typical chemical compounds regarding the biological activity A. Likewise, The exemplars B1-B3 all match the specified biological activity B and the hopeful chemical compound space 1708 is a region with small distances from all the coordinates of the feature vectors of the three exemplars and includes coordinates of feature vectors of typical chemical compounds regarding the biological activity B.

The hopeful chemical compound spaces 1707 and 1708 includes, respectively, 3 and 2 similar chemical compounds for which there is no biological activity information (circular points) and 0 and 1 similar chemical compounds for which there is biological activity information (square points). Accordingly, respective biological activity information existence rates are 0% and 33%.

The hopeful chemical compound space 1709 is a region with small distances from both the coordinate of the feature vector of the exemplar A1 matching the biological activity A and the coordinate of the feature vector of the exemplar B1 matching the biological activity B and includes coordinates of feature vectors of similar chemical compounds common to the two biological activities (e.g. multiple biological activity chemical compounds).

Also, the hopeful chemical compound space 1710 is a region with small distances from both the coordinate of the feature vector of the exemplar A2 matching the biological activity A and the coordinate of the feature vector of the exemplar B2 matching the biological activity B and includes coordinates of feature vectors of similar chemical compounds common to the two biological activities (e.g. multiple biological activity chemical compounds).

The hopeful chemical compound spaces 1709 and 1710 include, respectively, 5 and 4 similar chemical compounds for which there is no biological activity information (circular points) and 0 and 3 similar chemical compounds for which there is biological activity information (square points). Accordingly, respective biological activity information existence rates are 0% and 43%.

By adding an unknown differential feature amount to the exemplar B3, the hopeful chemical compound space 1706 including the similar chemical compounds for the exemplar B3 translates to the hopeful chemical compound space 1711 in response to the added differential feature amount. Likewise, the hopeful chemical compound space 1708 including the typical chemical compounds translates to the hopeful chemical compound space 1712 in response to the differential feature amount and the hopeful chemical compound space 1709 including the multiple biological activity chemical compounds translates to the hopeful chemical compound space 1713 in response to the differential feature amount.

The user repeats searches for new region spaces with high prospect by specifying exemplar chemical compounds and differential feature amounts based on experience and inspiration while adjusting, little by little, positions of hopeful chemical compound region spaces including multiple biological activity chemical compounds combining a plurality of exemplar chemical compounds or positions of hopeful chemical compound region spaces translated in response to the differential feature amounts. Regions with a high prospect may be searched automatically by automating the specifying process of the exemplar chemical compound and the differential feature amounts by a method such as a round-robin algorithm for combinations or array values. Methods for manually or automatically searching regions with a high prospect by repeating searches for regions wherein feature vectors of a plurality of exemplar chemical compounds are combined or searches for regions changed partially by the differential feature amounts attempt to reproduce the methods wherein creatures evolved to species more advantageous for survival by combining DNA sequences of a male and a female or changing the DNA sequence partially by mutation and to reproduce human intuition or creativity fix producing a new concept by combining different types of data.

In the above embodiments, the control lines and information lines indicate those considered to be necessary for explanation but do not always indicate all control lines or information lines in a product. All constructions may be connected to each other.

DESCRIPTION OF SYMBOLS

100 Search System
102,700,900,1100,1400,1500,1600 GUI
109 Search Module (Chemical Compound Searcher)
300 Exemplar Table
305 Ring Structure Information (Information representing Structural Features)
306 Chain Structure Information (Information representing Structural Features)
307 Physical/Chemical Feature Information
308 Biological Activity Information
354 Pharmacophore Information (Information representing Structural Features)
400 Search Table
710 Similar Chemical Compound Biological Activity Information Existence Rate
720 Existence Rate Deviation

What is claimed is:

1. A computer executing a search system for a chemical compound having a biological activity, the computer comprising:
a first processor coupled to a storage medium,
wherein the storage medium stores a search table and an exemplar table, the search table and the exemplar table record information representing structural features or physical/chemical features for a plurality of chemical compounds, and wherein the search table and the exemplar table further record information representing a biological activity including a biological response or a biological effect level;
wherein the first processor is programmed to execute a chemical compound searcher, wherein the chemical compound searcher:
obtains at least one chemical compound as a specified chemical compound based on the chemical compounds recorded on the exemplar table;
obtains feature vectors representing the structural features or the physical/chemical features for the specified chemical compound and the chemical compound recorded on the search table;
calculates a feature vector distance between the feature vector of the specified chemical compound and each chemical compound recorded on the search table; and
obtains a chemical compound recorded on the search table as a similar chemical compound in response to the feature vectors distances,
wherein the first processor is connected to a second processor that executes a graphical user interface (GUI) for displaying the similar chemical compound and information representing a biological activity of the similar chemical compound,
wherein, upon obtaining the specified chemical compound, the chemical compound searcher:
obtains a specified biological activity;
obtains one or more chemical compounds recorded on the exemplar table whose biological activities match the specified biological activity as the specified chemical compounds; and
obtains the similar chemical compound for which a sum or an average of the feature vectors distances to the specified chemical compounds is smallest as a typical chemical compound, and
wherein the GUI displays information for identifying the typical chemical compound upon displaying the similar chemical compound.

2. The computer executing the search system for a chemical compound having a biological activity according to claim 1, wherein:
the structural features include a number regarding ring structures, a number regarding chain structures or a number regarding pharmacophores;
the physical/chemical features include molar mass, boiling point, freezing point, vapor pressure, density, water solubility, organic solvent solubility, thermal stability, acidity/alkalinity or spectrum; and
the GUI displays a plurality of the similar chemical compounds in an ascending order of the feature vectors distance.

3. The computer executing the search system for a chemical compound having a biological activity according to claim 1, wherein:
the chemical compound searcher changes weight values of respective elements in the feature vectors within a range including an interval from 0 to 2, inclusive, upon calculating the feature vectors distances.

4. The computer executing the search system for a chemical compound having a biological activity according to claim 1,
wherein the GUI further displays a graph screen;

wherein in the graph screen, the specified chemical compound and the similar chemical compound are displayed as nodes of respectively different colors; and wherein a length or a thickness of a line connecting the node of the specified chemical compound and the node of the similar chemical compound is determined based on their feature vectors distance.

5. The computer executing the search system for a chemical compound having a biological activity according to claim 1, wherein the chemical compound searcher obtains the information representing the difference in the structural features as a sequence including numerical values having positive or negative signs.

6. The computer executing the search system for a chemical compound having a biological activity according to claim 1, wherein the chemical compound searcher calculates an existence rate deviation based on:

a similar chemical compound biological activity information existence rate representing a ratio of the similar chemical compounds for which information representing any biological activity is recorded to all the similar chemical compounds;

a total biological activity information existence rate representing a ratio of the chemical compounds recorded on the search table for which any information representing biological activity is recorded to all the chemical compounds recorded on the search table, and wherein the GUI displays the existence rate deviation.

7. The computer executing the search system for a chemical compound having a biological activity according to claim 1, wherein the chemical compound searcher calculates the feature vectors distance by:

squaring differences between feature amounts included in the respective feature vectors and summing them; or squaring differences between feature amounts included in the respective feature vectors, summing them and taking a square root thereof.

8. A computer executing a search system for a chemical compound having a biological activity, the computer comprising:

a first processor coupled to a storage medium, wherein the storage medium stores a search table and an exemplar table, the search table and the exemplar table record information representing structural features or physical/chemical features for a plurality of chemical compounds, and wherein the search table and the exemplar table further record information representing a biological activity including a biological response or a biological effect level;

wherein the first processor is programmed to execute a chemical compound searcher, wherein the chemical compound searcher:

obtains at least one chemical compound as a specified chemical compound based on the chemical compounds recorded on the exemplar table;

obtains feature vectors representing the structural features or the physical/chemical features for the specified chemical compound and the chemical compound recorded on the search table;

calculates a feature vector distance between the feature vector of the specified chemical compound and each chemical compound recorded on the search table; and obtains a chemical compound recorded on the search table as a similar chemical compound in response to the feature vectors distances, and wherein the first processor is connected to a second processor that executes a graphical user interface (GUI) for displaying the similar chemical compound and information representing a biological activity of the similar chemical compound, wherein, upon obtaining the specified chemical compound, the chemical compound searcher:

obtains a distance threshold;

obtains a first specified biological activity and a second specified biological activity;

obtains one or more chemical compounds whose biological activities match the first specified biological activity among the chemical compounds recorded on the exemplar table as first specified chemical compounds;

obtains one or more chemical compounds whose biological activities match the second specified biological activity among the chemical compounds recorded on the exemplar table as second specified chemical compounds; and wherein the chemical compound searcher further obtains the chemical compounds, among the similar chemical compounds, for which a sum or an average of the feature vectors distances to the first specified chemical compounds are equal to or less than the distance threshold and a sum or an average of the feature vectors distances to the second specified chemical compounds are equal to or less than the distance threshold as multiple biological activity chemical compounds, and wherein the GUI displays information for identifying the multiple biological activity chemical compound upon displaying the similar chemical compound.

9. The computer executing the search system for a chemical compound having a biological activity according to claim 8, wherein the structural features include a number regarding ring structures, a number regarding chain structures or a number regarding pharmacophores, wherein the physical/chemical features include molar mass, boiling point, freezing point, vapor pressure, density, water solubility, organic solvent solubility, thermal stability, acidity/alkalinity or spectrum, and wherein the GUI displays a plurality of the similar chemical compounds in an ascending order of the feature vectors distance.

10. The computer executing the search system for a chemical compound having a biological activity according to claim 8, wherein the chemical compound searcher changes weight values of respective elements in the feature vectors within a range including an interval from 0 to 2, inclusive, upon calculating the feature vectors distances.

11. The computer executing the search system for a chemical compound having a biological activity according to claim 8, wherein the GUI further displays a graph screen, wherein in the graph screen, the specified chemical compound and the similar chemical compound are displayed as nodes of respectively different colors, and wherein a length or a thickness of a line connecting the node of the specified chemical compound and the node of the similar chemical compound is determined based on their feature vectors distance.

12. The computer executing the search system for a chemical compound having a biological activity according to claim 8,
wherein the chemical compound searcher obtains the information representing the difference in the structural features as a sequence including numerical values having positive or negative signs.

13. The computer executing the search system for a chemical compound having a biological activity according to claim 8, wherein the chemical compound searcher calculates an existence rate deviation based on:
a similar chemical compound biological activity information existence rate representing a ratio of the similar chemical compounds for which information representing any biological activity is recorded to all the similar chemical compounds;
a total biological activity information existence rate representing a ratio of the chemical compounds recorded on the search table for which any information representing biological activity is recorded to all the chemical compounds recorded on the search table, and
wherein the GUI displays the existence rate deviation.

14. The computer executing the search system for a chemical compound having a biological activity according to claim 8, wherein the chemical compound searcher calculates the feature vectors distance by:
squaring differences between feature amounts included in the respective feature vectors and summing them; or
squaring differences between feature amounts included in the respective feature vectors, summing them and taking a square root thereof.

15. A computer executing a search system for a chemical compound having a biological activity, the computer comprising:
a first processor coupled to a storage medium,
wherein the storage medium stores a search table and an exemplar table, the search table and the exemplar table record information representing structural features or physical/chemical features for a plurality of chemical compounds, and wherein the search table and the exemplar table further record information representing a biological activity including a biological response or a biological effect level;
wherein the first processor is programmed to execute a chemical compound searcher, wherein the chemical compound searcher:
obtains at least one chemical compound as a specified chemical compound based on the chemical compounds recorded on the exemplar table;
obtains feature vectors representing the structural features or the physical/chemical features for the specified chemical compound and the chemical compound recorded on the search table;
calculates a feature vector distance between the feature vector of the specified chemical compound and each chemical compound recorded on the search table; and
obtains a chemical compound recorded on the search table as a similar chemical compound in response to the feature vectors distances,
wherein the first processor is connected to a second processor that executes a graphical user interface (GUI) for displaying the similar chemical compound and information representing a biological activity of the similar chemical compound,
wherein, upon obtaining the specified chemical compound, the chemical compound searcher:
obtains a chemical compound recorded on the search table and information representing a difference in the structural features;
obtains the specified chemical compound by applying the difference to the structural features of the chemical compound recorded on the search table; and
wherein the chemical compound searcher further:
further obtains the feature vectors for the chemical compounds recorded on the exemplar table;
calculates the feature vectors distance between the feature vector of the specified chemical compound and the feature vector of each chemical compound recorded on the exemplar table; and
obtains at least one chemical compound recorded on the exemplar table or the search table in response to the feature vectors distances upon obtaining the similar chemical compound.

16. The computer executing the search system for a chemical compound having a biological activity according to claim 15,
wherein the structural features include a number regarding ring structures, a number regarding chain structures or a number regarding pharmacophores,
wherein the physical/chemical features include molar mass, boiling point, freezing point, vapor pressure, density, water solubility, organic solvent solubility, thermal stability, acidity/alkalinity or spectrum, and
wherein the GUI displays a plurality of the similar chemical compounds in an ascending order of the feature vectors distance.

17. The computer executing the search system for a chemical compound having a biological activity according to claim 15,
wherein the chemical compound searcher changes weight values of respective elements in the feature vectors within a range including an interval from 0 to 2, inclusive, upon calculating the feature vectors distances.

18. The computer executing the search system for a chemical compound having a biological activity according to claim 15,
wherein the GUI further displays a graph screen,
wherein in the graph screen, the specified chemical compound and the similar chemical compound are displayed as nodes of respectively different colors, and
wherein a length or a thickness of a line connecting the node of the specified chemical compound and the node of the similar chemical compound is determined based on their feature vectors distance.

19. The computer executing the search system for a chemical compound having a biological activity according to claim 15,
wherein the chemical compound searcher obtains the information representing the difference in the structural features as a sequence including numerical values having positive or negative signs.

20. The computer executing the search system for a chemical compound having a biological activity according to claim 15, wherein the chemical compound searcher calculates an existence rate deviation based on:
a similar chemical compound biological activity information existence rate representing a ratio of the similar chemical compounds for which information representing any biological activity is recorded to all the similar chemical compounds;
a total biological activity information existence rate representing a ratio of the chemical compounds recorded on the search table for which any information representing biological activity is recorded to all the chemical compounds recorded on the search table, and wherein the GUI displays the existence rate deviation.

21. The computer executing the search system for a chemical compound having a biological activity according to claim 15, wherein the chemical compound searcher calculates the feature vectors distance by:

squaring differences between feature amounts included in the respective feature vectors and summing them; or squaring differences between feature amounts included in the respective feature vectors, summing them and taking a square root thereof.

* * * * *